(12) United States Patent
Scott

(10) Patent No.: US 10,070,987 B2
(45) Date of Patent: Sep. 11, 2018

(54) MEDICAL DEVICE, METHOD OF MAKING AND USING THE SAME

(71) Applicant: James Gordon Scott, Guffey, CO (US)

(72) Inventor: James Gordon Scott, Guffey, CO (US)

(*) Notice: Subject to any disclaimer, the term of this patent is extended or adjusted under 35 U.S.C. 154(b) by 729 days.

(21) Appl. No.: 14/205,868

(22) Filed: Mar. 12, 2014

(65) Prior Publication Data

US 2014/0276500 A1    Sep. 18, 2014

Related U.S. Application Data

(60) Provisional application No. 61/778,376, filed on Mar. 12, 2013.

(51) Int. Cl.
*A61F 5/44* (2006.01)
*A61F 5/449* (2006.01)

(52) U.S. Cl.
CPC ............ *A61F 5/449* (2013.01); *A61F 5/4404* (2013.01); *Y10T 29/49826* (2015.01)

(58) Field of Classification Search
CPC combination set(s) only.
See application file for complete search history.

(56) References Cited

U.S. PATENT DOCUMENTS

| | | | | |
|---|---|---|---|---|
| 1,922,763 A * | 8/1933 | Gricks | ................... | A61F 5/445 604/340 |
| 2,127,834 A * | 8/1938 | Spindell | ................. | A61F 5/449 604/345 |
| 2,314,724 A * | 3/1943 | Marsan | ................... | A61F 5/445 138/37 |
| 2,496,175 A * | 1/1950 | Perry | ..................... | A61F 5/445 604/335 |
| 2,549,649 A * | 4/1951 | Van Hove | .............. | A61F 5/445 604/341 |
| 2,656,838 A * | 10/1953 | McConnell | ............ | A61F 5/445 604/340 |
| 2,675,001 A * | 4/1954 | Jones | .................... | A61F 5/445 604/343 |
| 2,675,002 A * | 4/1954 | Cesare | ................... | A61F 5/445 604/338 |
| 2,895,476 A * | 7/1959 | Hallard | .................. | A61F 5/449 604/400 |
| 3,074,404 A * | 1/1963 | Robinson | ............... | A61F 5/448 604/338 |
| 3,076,458 A * | 2/1963 | Mason | ................... | A61F 5/448 604/339 |
| 3,283,757 A * | 11/1966 | Nelson | ................... | A61F 5/448 604/334 |
| 3,398,744 A * | 8/1968 | Hooper | .................. | A61F 5/445 604/340 |
| 3,762,412 A * | 10/1973 | Frank | ..................... | A61F 5/448 604/338 |
| 3,773,048 A * | 11/1973 | Kirkliauskas | .......... | A61F 5/445 604/345 |

(Continued)

*Primary Examiner* — Tatyana Zalukaeva
*Assistant Examiner* — Guy K Townsend
(74) *Attorney, Agent, or Firm* — Aspire IP, LLC; Scott J. Hawranek

(57) ABSTRACT

An ostomy armor includes a rigid base plate that covers a stoma of a patient and at least a portion of a waste collection bag attached to the stoma. The ostomy armor further includes a plate pad attached to the back surface of the rigid base plate. The ostomy armor also includes a belt that to hold the ostomy armor on the patient.

27 Claims, 24 Drawing Sheets

(56) References Cited

U.S. PATENT DOCUMENTS

| | | | | |
|---|---|---|---|---|
| 4,596,566 | A * | 6/1986 | Kay | A61F 5/445 |
| | | | | 604/176 |
| 4,636,206 | A * | 1/1987 | Ederati | A61F 5/4404 |
| | | | | 604/340 |
| 4,723,952 | A * | 2/1988 | Esposito | A61F 5/448 |
| | | | | 604/338 |
| 5,013,307 | A | 5/1991 | Broida | |
| 5,178,614 | A * | 1/1993 | McDowell | A61F 5/445 |
| | | | | 604/332 |
| 5,209,744 | A * | 5/1993 | Abe | A61F 5/445 |
| | | | | 604/332 |
| 5,338,315 | A * | 8/1994 | Baker | A61F 5/445 |
| | | | | 128/888 |
| 5,478,334 | A * | 12/1995 | Bernstein | A61F 5/448 |
| | | | | 604/345 |
| 5,626,570 | A * | 5/1997 | Gallo | A61F 5/449 |
| | | | | 2/49.2 |
| 5,679,399 | A * | 10/1997 | Shlenker | A61B 42/10 |
| | | | | 128/844 |
| 6,129,715 | A * | 10/2000 | Cunningham | A61F 5/445 |
| | | | | 128/885 |
| 6,328,721 | B1 | 12/2001 | Prohaska | |
| 7,540,861 | B1 * | 6/2009 | Voto | A61F 5/443 |
| | | | | 604/343 |
| 7,935,097 | B1 * | 5/2011 | Moore | A61F 5/449 |
| | | | | 604/333 |
| 2005/0256466 | A1 * | 11/2005 | Winkler | A61F 5/449 |
| | | | | 604/337 |
| 2007/0135783 | A1 | 6/2007 | Scott | |
| 2009/0182191 | A1 * | 7/2009 | Redlich | A61F 5/445 |
| | | | | 600/32 |

* cited by examiner

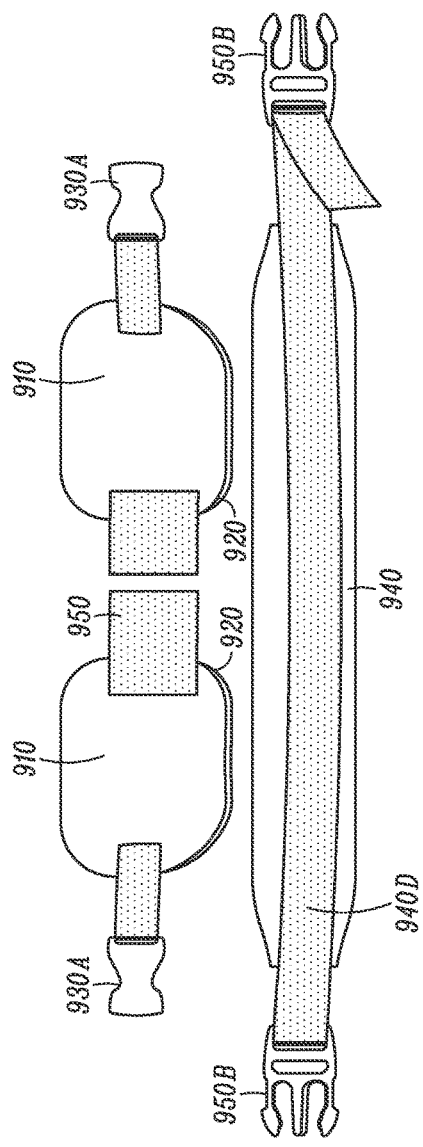
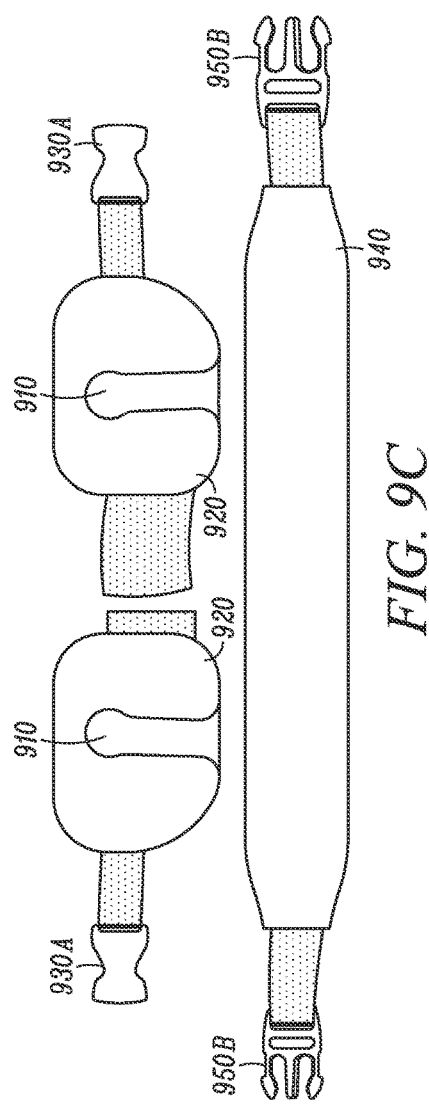
FIG. 9B
FIG. 9C

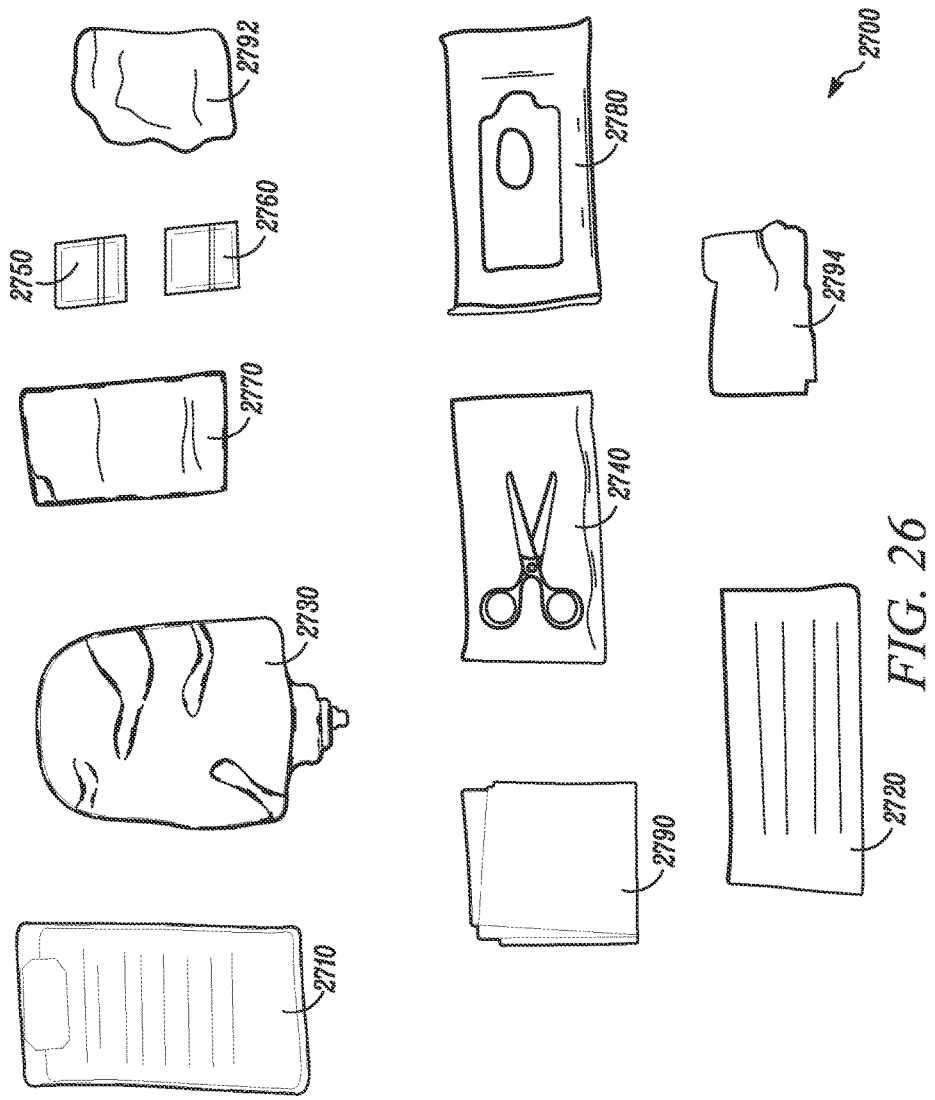

MEDICAL DEVICE, METHOD OF MAKING AND USING THE SAME

CROSS REFERENCE TO RELATED APPLICATION

This application claims the benefit of U.S. Provisional Application No. 61/778,376, filed Mar. 12, 2013, the content of which is fully incorporated by reference herein.

BACKGROUND OF THE INVENTION

Field of the Invention

The present invention generally relates to a medical device for ostomy sites or stoma, and more particularly to a device, method of using, and system for protecting the patient and the patient's ostomy sites.

Description of the Related Art

An ostomy pouching system (bag) is a medical device that provides for collecting waste from a stoma, a surgically created opening that connects a body cavity to outside the body. An ostomy bag is often used with stoma resulting from procedures such as colostomies, ileostomies, and urostomies, where the stoma may be placed at the abdomen of the person who received the procedure.

An ostomy pouching system typically includes a skin barrier or wafer (faceplate) and a collection pouch. The pouch attaches to the abdomen by the skin barrier and is fitted over and around the stoma to collect the output of the body, which is usually stool or urine. The skin barrier protects the skin from the stoma output while being collected in the bag.

An ostomy pouching system may consist of one piece or two pieces. In a one-piece system, the skin barrier and the pouch are joined together as a single unit. The one-piece system provides simplicity in design but requires changing the entire unit, including the skin barrier, when the pouch requires changing. A two-piece system leaves the skin barrier attached to the skin at the changing of the pouch. In a two-piece system, the skin barrier may be part of a flange unit, where the pouch includes a closed ring that attaches mechanically to a mating piece on the flange when the pouch is joined with the skin barrier. A common connection mechanism may consist of a pressure fit snap ring.

Pouches in an ostomy pouching system may be open-ended or closed-ended. In an open-ended pouch, the pouch is opened at the bottom and may be sealed by a closing device, such as a clamp or tail clip. During emptying of the content collected in the pouch, the open-ended pouch may stay attached to the body of the person and is emptied by draining and may be reused. In a close-ended pouch, the bottom of the pouch is closed and sealed. Close-ended pouches are generally discarded after one use.

A feeding tube is a medical device that is surgically implanted into a person that allows nutrient substances to be fed into the body of the person. A feeding tube may include gastric, jejunostomy, and gastrojejunostomy feeding tube that are inserted into the abdomen and allows access to a combination of the stomach and the jejunum.

There are deficiencies with the related art. For example, the pouch of an ostomy pouching system is generally non-rigid and has a risk to being pierced or punctured. The content collected by the pouch, which may include stool and urine, are undesirable. A leak of the content in the pouch while a person is wearing the pouch, i.e., when the pouch is punctured, may lead to embarrassment and other social disproval for the wearer of the pouch. As such, a person needing the wear an ostomy pouching system may be lead to avoid activities that may increase the risks that the pouch would leak or puncture. In another example, spills and leakage of the pouch may still occur due to other reasons, i.e., accidents or unexpected circumstances. Leakage for any reason will lead to the same embarrassment or social disproval for the wearer.

Also, both the ostomy pouching system and the feeding tube are important life support devices for the wearer. It would further be advantageous to improve the security and the robustness of these devices while reducing the hindrance of these devices to everyday life of the wearer.

SUMMARY OF THE INVENTION

Accordingly, the invention is directed to a medical device, method of making, and using the same as a protection system for ostomies that substantially obviates one or more of the problems due to limitations and disadvantages of the related art.

An advantage of the invention is to eliminate or minimize all known drawbacks to living life with an ostomy, allowing for a normal and wide range of motion and allowing formerly active individuals to return to normal activity after ostomy surgery.

Another advantage of the invention is to provide protection for the abdominal wall or stomal site from blunt-force trauma, and for appliance integrity.

Yet another advantage of the invention is to prevent or minimize herniation of a stoma or ostomy site and accommodate existing hernias.

Still yet another advantage of the invention is the device is configured to prevent or minimize herniation, leaks, blowouts, and make the protection system resilient against impact damage.

Yet still another advantage of the invention is the device conforming to the abdominal region as well as facilitated for protection, comfort, and maintenance of wearing the system. The device is also thin and discreet to other people.

Further advantage of the invention is the device directly covers an ostomy appliance and pouch and is normally worn next to the skin. When worn correctly, the device is snug, but comfortable.

Another further advantage of the invention is the device is fully submersible in water and provides it's normal protection while swimming or waterskiing.

Yet another further advantage of the invention is the device is TSA approved for wear on board commercial airline flights.

Additional features and advantages of the invention will be set forth in the description which follows, and will be apparent from the description, or may be learned by practice of the invention. The objectives and other advantages of the invention will be realized and attained by the structure particularly pointed out in the written description and claims hereof as well as the appended figures.

According to an embodiment, a medical apparatus includes a rigid base plate configured to cover a stoma of a user and at least a portion of a waste collection bag attached to the stoma, a plate pad coupled to a back surface of the rigid base plate, and a belt configured to hold the medical apparatus on the user.

According to an embodiment, a method of making an ostomy apparatus includes preparing a rigid base plate configured to cover a stoma of a user and at least a portion of a waste collection bag attached to the stoma, attaching a plate pad to a back of the rigid base plate, and connecting a belt to the ostomy apparatus.

According to an embodiment, a medical apparatus includes a waste wick. The waste wick includes an absorbent material. The waste wick is shaped to fit between a flange and a pouch of a waste collection bag. The flange includes a skin barrier configured to attach to a stoma of a user, collect waste material from the stoma, and fill the pouch with the waste material. The absorbent material is configured to absorb the waste material that leaked from the waste collection bag.

According to an embodiment, a medical apparatus includes a rigid plate face configured to cover a waste collection bag for a stoma of a user. The rigid base plate comprises a raised channel, a side plate surrounding the raised channel, and a protective area below the raised channel. The medical apparatus further includes a plate pad coupled to the side plate of a back of the rigid plate face. The plate pad comprises a cutout at the raised channel portion providing access to a back of the raised channel.

According to an embodiment, a medical apparatus includes a recessed portion configured to receive a feeding tube from a body of a user. The feeding tube is guided from an entrance space of the recessed portion to an opening at a side of the medical apparatus.

According to an embodiment, a method of using a feeding tube armor includes guiding a feeding tube from a body of the user through an entrance space of a recessed portion of the feeding tube armor, and guiding the feeding tube through an opening at a side of the feeding tube armor.

According to an embodiment, a medical apparatus includes a feeding tube armor. The feeding tube armor includes a recessed portion configured to receive a feeding tube from a body of a user and a slit configured to receive an end of a buckle. The feeding tube is guided from an entrance space of the recessed portion to an opening at a side of the medical apparatus. The medical apparatus further includes an ostomy armor and a buckle configured to connect the feeding tube armor to the ostomy armor. An end of the buckle is configured to fit into a slit of the feeding tube armor and a second end of the buckle is configured to fit into a slit of the ostomy armor.

According to an embodiment, an ostomy appliance includes a customized three-dimensional structure for a stoma in a body of a user. The customized three-dimensional structure is constructed from a three-dimensional mold. The mold is substantially mapped from a three-dimensional contour of the stoma and an area around the stoma.

According to an embodiment, a method of making an ostomy appliance includes mapping a three-dimensional contour of a stoma in a body of a user and an area around the stoma, creating a three-dimensional mold from the mapped three-dimensional contour, and making the ostomy appliance as a customized three-dimensional structure based on the three-dimensional mold.

According to an embodiment, a medical apparatus includes a waste collection bag, an opening on a portion of the bag configured to receive fluid from a stoma on a body of a user, and a raised ridge extending from the opening to an end of the bag.

According to an embodiment, an emergency medical kit for treating one or more of ileostomy, colostomy, and urostomy leaks, changes, and blowouts, includes a contents container configured to compactly store contents and one or more of (a)-(i) stored in the contents container: (a) a waste collection appliance for collecting one or more of urine and solid waste; (b) a scissor; (c) an adhesive removal wipe; (d) a waste appliance preparation wipe; (e) a paper towel; (f) a baby wipe; (g) a disposable apron; (h) a pair of disposable gloves; (i) a trash bag; and (j) instructions for using the contents container and the contents of the contents container.

According to an embodiment, a method of preparing an emergency medical kit for treating one or more of ileostomy, colostomy, and urostomy leaks, changes, and blowouts includes preparing a contents container configured to compactly store contents and one or more of (a)-(i) stored in the contents container: (a) a waste collection appliance for collecting one or more of urine and solid waste; (b) a scissor; (c) an adhesive removal wipe; (d) a waste appliance preparation wipe; (e) a paper towel; (f) a baby wipe; (g) a disposable apron; (h) a pair of disposable gloves; (i) a trash bag; and (j) instructions for using the contents container and the contents of the contents container.

According to an embodiment, a method of using an emergency medical kit for treating one or more of ileostomy, colostomy, and urostomy leaks, changes and blowouts includes opening a contents container configured to compactly store contents, cleaning the leaks, changes, and blowouts using one or more contents in the kit, and replacing a waste collection appliance of ileostomy, colostomy, and urostomy using the waste collection appliance in the kit. One or more of (a)-(i) is stored in the contents container: (a) the waste collection appliance for collecting one or more of urine and solid waste; (b) a scissor; (c) an adhesive removal wipe; (d) a waste appliance preparation wipe; (e) a paper towel; (f) a baby wipe; (g) a disposable apron; (h) a pair of disposable gloves; (i) a trash bag; and (j) instructions for using the contents container and the contents of the contents container.

It is to be understood that both the foregoing general description and the following detailed description are exemplary and explanatory and are intended to provide further explanation of the invention as claimed.

The phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising," "including," and "having" can be used interchangeably.

The term "bag," "pouch," or other similar terms refer to a rigid or non-rigid container. Specifically, the term "waste collection bag" refers to a container configured for collecting waste, i.e., biowaste collected from a human body from a stomal opening.

The term "armor," "plate," or similar terms refers to a covering configured to protect an object, i.e., a stoma, from one or more of an external or internal objects, actions, environments, or other physical or non-physical disturbance to the protected object. The covering may be rigid or non-rigid and may be of a single piece or of a combination of pieces and/or systems.

The term "belt" refers to a flexible or non-flexible band, strap, or other similar objects configured to be worn around a human body. A belt may be use to secure or carry an object on the human body, i.e., an ostomy armor that is connected to the belt. A belt may include buckles that may be adjustable or removable to further secure the belt to the human body. A "buckle" refers to one or more connecting and/or locking mechanisms. A buckle may be part of the belt and may split the belt into two or more pieces when the buckle is disconnected, which may facilitate the user in removing the belt. A buckle may also include one or more pieces that connects two or more objects without being connected to a belt. A belt may also be one or more whole pieces without any buckle and may be removed or secured by other means, i.e., the belt is made of stretchable materials that is worn or removed on the human body by stretching. A belt may also include other pieces and accessories such as padding in certain portions of the belt that improves the comfort, stability, or other properties when the person wears the belt.

The term "pad" refers to a mass that has a relative property of providing one or more of comfort, protection, and other similar properties against another material acting on a human body. A pad may be soft and cushion-like or may be hard, i.e., a hard material that has a relatively compressible property when acted upon by a force in comparison with another material. A pad may have an absorbent or non-absorbent property. A pad may be fitted by a covering on the outside, at which the covering and the material inside the covering may be considered the entire pad. For example, a pad may contain an air-tight covering filled with air, water, or other materials.

The term "mold" refers to a pattern or model configured for producing or shaping a material to a final object. A mold may include two or three-dimensional pattern or model and may be rigid or non-rigid. A mold may take on substantially the same shape as the modeled object or may include other offsets (i.e., dimensionally in width, length, and height) or morphing and may contain more or less detail than the modeled object. A mold may also include computer or other digital models, where the final object is produced through direct construction (i.e., 3D printing) without using a physical mold. A mold may include various stages of a mold (i.e., positive and negative molds and reinforced molds). Final objects produced from a mold may be devices and objects used for a customized fit for the modeled object.

It shall be understood that the term "means," as used herein, shall be given its broadest possible interpretation in accordance with 35 U.S.C., Section 112(f). Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The preceding is a simplified summary of the disclosure to provide an understanding of some aspects of the disclosure. This summary is neither an extensive nor exhaustive overview of the disclosure and its various aspects, embodiments, and/or configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and/or configurations of the disclosure are possible, utilizing, alone or in combination, one or more of the features set forth above or described in detail below.

BRIEF DESCRIPTION OF THE FIGURES

The accompanying figures, which are included to provide a further understanding of the invention are incorporated in and constitute a part of this specification, illustrate embodiments of the invention and together with the description serve to explain the principles of the invention.

FIGS. 9A, 9B, and 9C illustrate exemplary views of a dual ostomy armor according to an embodiment;

FIG. 26 illustrates an exemplary view of an emergency leak and blowout kit (EBOK) according to an embodiment.

DETAILED DESCRIPTION OF THE PREFERRED EMBODIMENTS

Embodiments of the invention are configured for various physiologies and appliances, to prevent herniation, leaks, blowouts, and make a protection system resilient against impact damage. The device is configured for holding and protection of the stoma and bag system in place. Moreover, embodiments of the invention are directed towards an apparatus for protection, comfort, and maintenance of wearing the system.

Reference will now be made in additional detail to an embodiment of the present invention, example of which is illustrated in the accompanying photographs.

Figure 1:
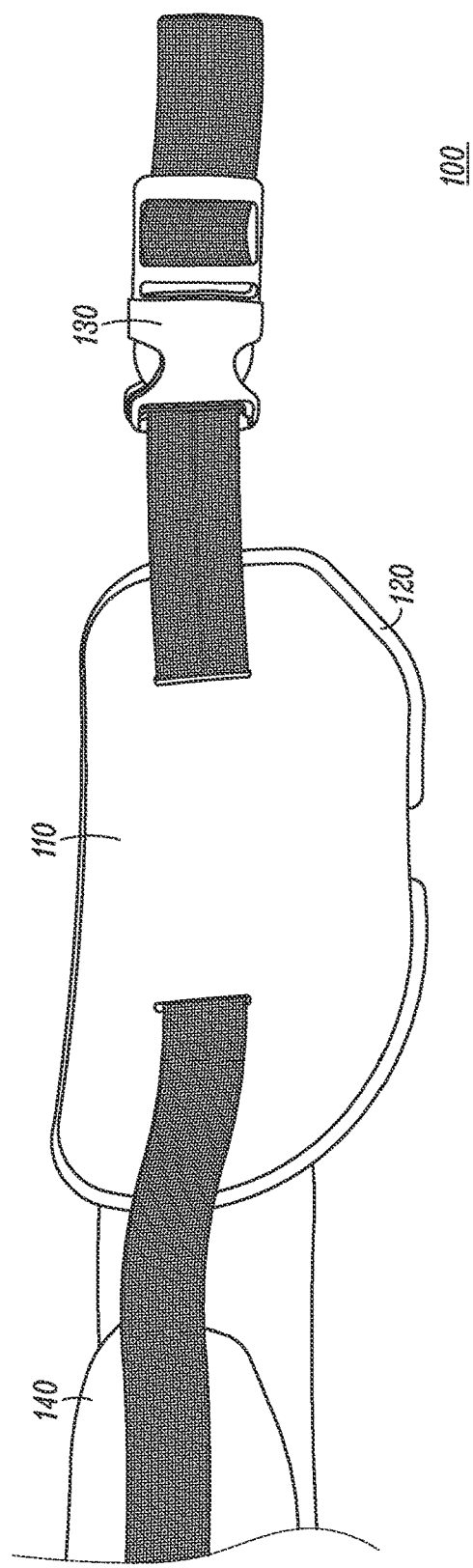
FIG. 1 illustrates an exemplary view of an ostomy armor according to an embodiment.

FIG. 1 illustrates an exemplary view of an ostomy armor according to an embodiment. Ostomy armor 100 includes a base plate 110 attached to a plate pad 120. Ostomy armor 100 also includes a belt, which includes a buckle 130 and a waist pad 140. The belt is fitted through two slits in the base plate 110 and provides support when a user wears the ostomy armor 100 over an ostomy.

In a preferred usage of the ostomy armor 100 according to an embodiment, the wearer may release the buckle 130 so that the belt would be unconnected from end to end, with the two pieces of the unconnected buckle 130 at each end of the belt. The plate pad 120 is positioned over the ostomy of the wearer such that the rigid base plate 110 faces the front away from the body of the wearer. The waist pad 140 may extend and wrap around over the back of the wearer, providing comfort to the wearer. The waist pad 140 and the extended belt portion containing one end of the buckle 130 wraps around from the back of the wearer to the front, where the other end of the buckle 130 is located. The belt may include an adjustable mechanism that lengthens or shortens the belt. The belt is pulled taught around the wearer's waist with the ostomy plate pad 120 positioned over the wearer's ostomy and may then be locked in place by connecting the two parts of buckle 130.

Each component of ostomy armor 100 and the making thereof is disclosed with respect to FIGS. 2-8.

Figure 2:
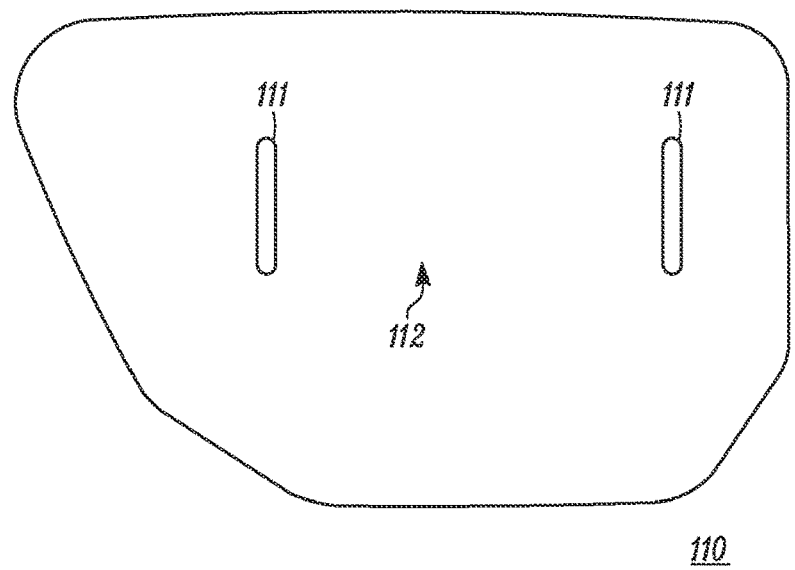
FIG. 2 illustrates an exemplary view of abdominal plate of the ostomy armor of FIG. 1.

FIG. 2 illustrates an exemplary view of base plate 110 of the ostomy armor of FIG. 1. Base plate 110 may be constructed from a metal material, alloy material, plastic material, fiber glass material, and combinations of the same. Base plate 110 may be rigid and strong to withstand impact from outside objects while protecting the contents beneath the base plate 110. In a preferred embodiment, the base plate 110 is constructed from an aircraft-grade aluminum. In the preferred embodiment, the material may be Aluminum 2024 T-3 0.032, 6061 T-6 0.020. In another embodiment, the plate may be constructed from carbon fiber/Kevlar™ (3/2 layup/mold or as needed), Kydex™ 0.040, injection molded ABS plastic, 0.025 Titanium, combination of the same, or other like materials.

Base plate 110 is formed to the desired dimension for the user. For example, the material of base plate 110 may be machined with a CNC, laser, or hand-cut, to a desired shape/dimension, e.g., standard shapes for adults, toddler, or other users. Generally, base plate 110 has a curved surface configured to be substantially similar to curvature of the abdominal area where the plate is covering. In addition, the outline shape of base plate 110 is configured to minimize pinching of the abdominal area when the plate is being used. In another embodiment, base plate 110 may also be custom made to conform to needs of the wearer, e.g., an obese user or a user with a unique body shape.

In an embodiment, base plate 110 includes slits 111 for receiving a belt including waist strap 140 as discussed with respect to FIG. 1. slits 111 consist of narrow holes cut directly from the base plate 110. Slits 111 are each cut at a distance from the edges of the base plate 110, oriented parallel to each other, and with width and height sufficient to accommodate inserting portions of a belt into the Slits 111 to loop around the wearer's waist. In another embodiment, slits 111 may be cut to various sizes, shapes, and orientation to accommodate various physiology of the wearer, i.e., an obese body shape or various nonconventional position of the stoma.

In an embodiment, base plate 110 includes a finishing. Base plate 110 may be finished with an anodized finish of various color. For example, base plate 110 may include a gold anodized finish, a combination of two color anodized wash finish, or other color and pattern combinations, i.e., an acid wash finish.

In an embodiment, base plate 110 includes marking 112. Marking 112 is imprinted on the face of the base plate 110. Marking 112 may be laser etched or imprinted on base plate 110 by other means now known or may be later derived in the art. The content of marking 112 may include various information, including the make, model, serial number, trademark, information and/or warning notices, and other information in various languages for the ostomy armor 100.

Figure 3:
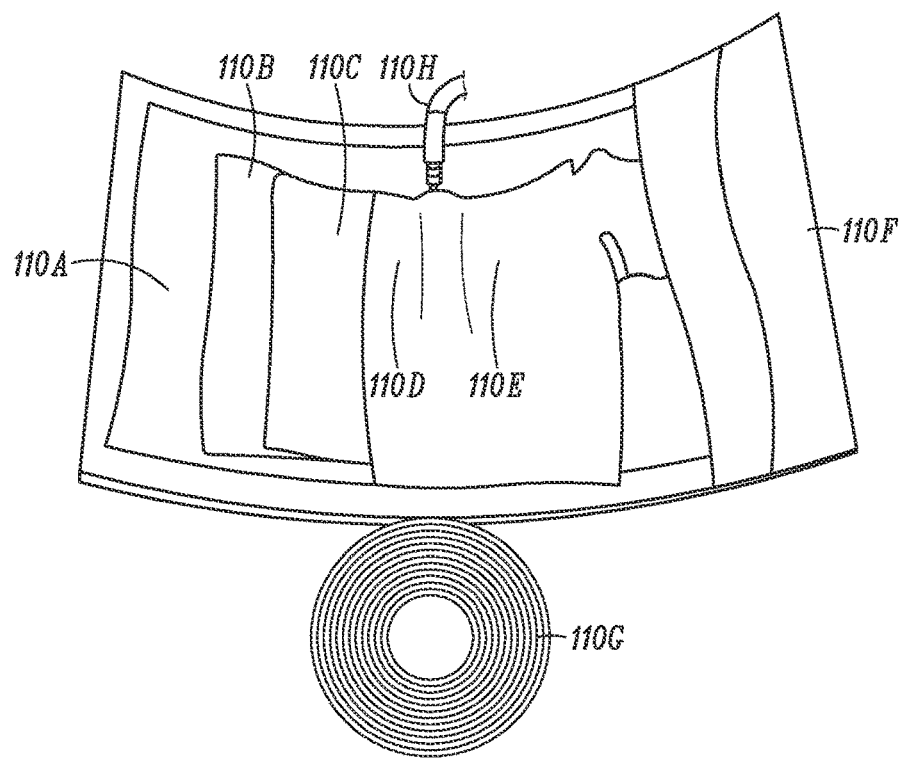
FIG. 3 illustrates an exemplary composition view of the base plate of the ostomy armor of FIG. 1.
Figure 4:
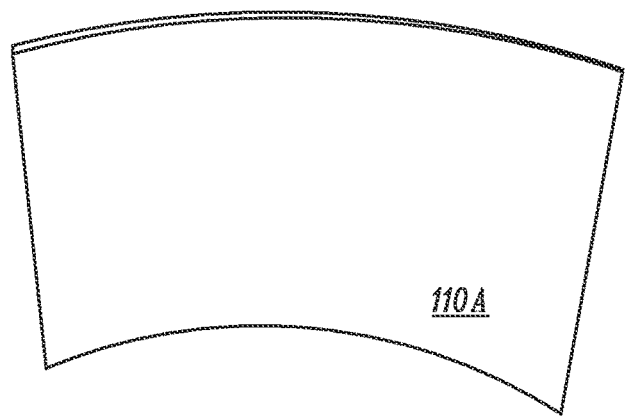
FIG. 4 illustrates an exemplary view of the base plate mold for making the ostomy armor of FIG. 1.

FIG. 3 illustrates an exemplary composition view of the base plate of the ostomy armor of FIG. 1. FIG. 4 illustrates an exemplary view of the base plate mold for making the ostomy armor of FIG. 1.

In an embodiment, base plate 110 may be constructed of any hard material, e.g., steel, aluminum, composite materials, combinations of the same, and other standard mold-making materials. Prior to or during, or after the construction of the base plate 110, the materials for the base plate 110 is shaped to approximate the curve of an abdominal wall of an average adult. In another embodiment, the base plate 110 materials may be shaped to with a custom curvature for a customized fit, i.e., toddlers, other parts of the body, or a person with a custom body shape.

In one embodiment, the base plate 110 is shaped to approximate the abdominal curve of an adult human by being formed in a mold 110A that is pre-shaped. In this embodiment, the mold 110A is constructed from common steel and rolled via mechanical means, e.g., using a standard slip roller. In another embodiment, other methods as now known or may be later derived of constructing a pre-shaped mold may be used.

The base plate mold 110A is used as a base layer to construct layers of composite materials for the base plate 110 according to an embodiment. For example, the base plate mold 110A is used as base layer for alternating layers of carbon fiber 110C and Kevlar™ 110B that serve as the composite materials for the base plate 110 in an exemplary embodiment. A thin layer of epoxy resin or other similar material may be used between the alternating layers of carbon fiber 110C and Kevlar™ 110B to hold the composite layers together. In an embodiment, the alternating layers are repeated until three layers of carbon fiber 110C is interspersed with two layers of Kevlar™ 110B. In another embodiment, other procedures may be used for the composite material as now known or may be later derived.

Other materials may also be used for the construction of base plate 110 in addition to the layers of carbon fiber 110C and Kevlar™ 110B. For example, other materials may include breather cloth 110D and peel ply 110E. Bagging film 110F, sealing compound 110G, and vacuum source 110H may be used to adhere or seal the composite materials used.

More specifically, base plate 110 may be constructed according to an embodiment as follows. First, the alternating layers of carbon fiber and Kevlar™ are prepared. A first layer of carbon fiber material 110C is placed directly on top of the base plate mold 110A. A resin material is placed on the carbon fiber material 110C. A first layer of Kevlar™, aramid fiber, or other structural material 110B is placed on the resin. A second layer of resin is placed on the Kevlar™ material 110B. A second layer of carbon fiber material 110C is placed on the first layer of Kevlar™ material 110B. A third layer of resin is placed on the second layer of carbon fiber material 110C. A fourth layer of resin is placed on the second layer of carbon fiber material 110C. A second layer of Kevlar™ material 110B is placed on the second layer of carbon fiber material 110C. A fifth layer of resin is placed on the second layer of Kevlar™ material 110B. A third layer of carbon fiber material is placed on the second layer of Kevlar™ material 110B.

Next, a peel-ply layer 110E is applied directly on top of the prepared alternating layers of carbon fiber 110C and Kevlar™ 110B. The peel-ply material may include a porous fabric. A breather cloth material 110D is applied on top of the peel-ply layer 110E. The breather cloth material 110D may include any fibrous material Next, the entire contents on the prepared base plate mold 110A are sealed in with a sealing tape 110G and a bagging film 110F. A vacuum is applied with tube 110H. In an embodiment, the vacuum pressure is about 15 mmHg, negative 15 PSI or greater. Optionally, heat may also be applied in the vacuuming process. The vacuum pressure is applied for about 2 hours or more, preferably 3 hours or more. The vacuum allows the resin to saturate the layers of carbon fiber 110C and Kevlar™ 110B. The excess resin is pulled into the breather cloth 110D and removed from the composite structure.

In another embodiment, the different layers of resin may not be needed as a previous layer of resin may bleed through. In a further embodiment, the number of layers of carbon fiber 104C may increase or decrease as the number of layers of carbon fiber material increases the overall rigidity of the final product is increased. Also, as the number of layers of Kevlar™ may increase or decrease as the number of layers of Kevlar™ increases the durability of the composite material. In another embodiment, other materials may be utilized to form the final composite material. The composite materials used may also be colored, e.g., red, green, blue, yellow, combinations of the same or other colors.

Next, the resultant shaped composite structure is removed from the base plate mold 110A.

In another embodiment, base plate mold 110A is substantially flat when the composite structure is formed in the mold. The resultant composite structure is then shaped to the size and curvature needed with techniques now known or may be later derived, e.g., machined, to form a desired geometry (the abdominal curve of an adult human).

In another embodiment, other forms of production of the base plate may be used, e.g., injection molded ABS plastic or Titanium, and 3D printing.

An exemplary method of making the base plate 110 according to an embodiment is as follows. Starting with a pre-shaped base plate mold 110A (shaped to a generic adult human abdomen), the base plate mold 110A is layered with composite materials such as carbon fiber 110C, Kevlar™ 110B, and/or other materials. The resulting shaped composite structure is removed from the base plate mold 110A. The shaped composite structure is cut (using laser or other methods) to a desired shape to form a base plate 110. Slits 111 are cut from the base plate 110. The base plate 110 may be further finished by anodization or other methods. Marking 112 may be imprinted or etched by laser or other means on the base plate 110.

In another embodiment, the method described is exemplary. Steps may be added or removed. For example, the finishing step or the marking step may be optional. Further, steps may be performed in different orders using different materials. For example, the shaping of the composite structure may be performed after the composite materials are layered on the back of flat base plate mold 110A.

Figure 5:
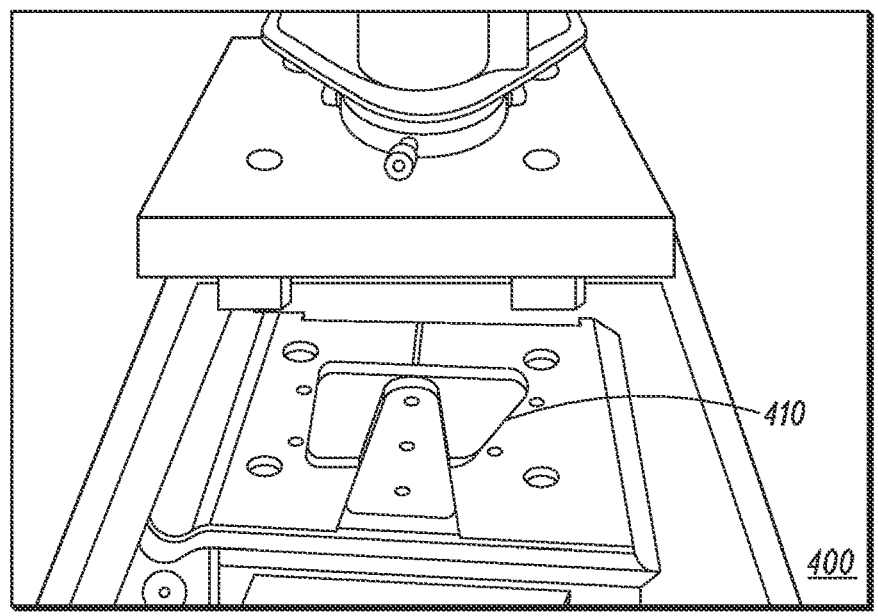
FIG. 5 illustrates an exemplary view of a manual arbor press and die cutting tool for producing a plate pad for the ostomy armor of FIG. 1.

FIG. 5 illustrates an exemplary view of a manual arbor press and die cutting tool for producing a plate pad for the ostomy armor of FIG. 1. Manual arbor press 400 uses a plate pad mold 410 to cut, form, and/or shape a plate pad 120 following the shape of the plate pad mold 410

Figure 6A:
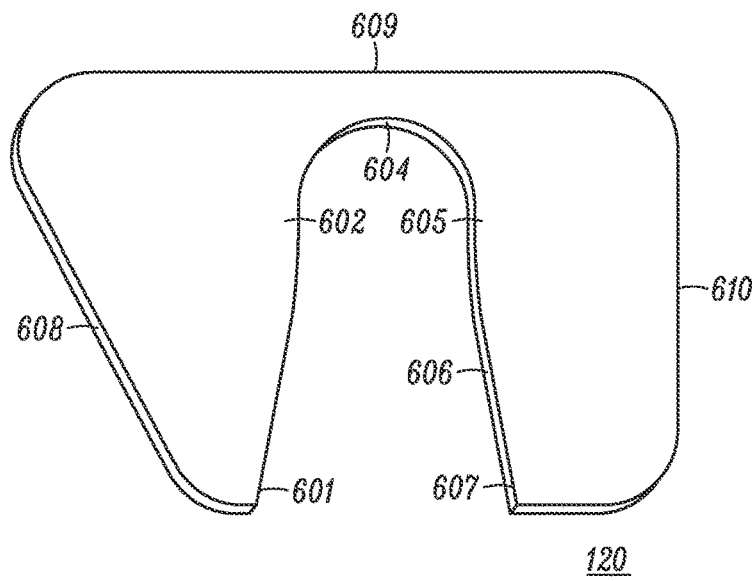
FIGS. 6A and 6B illustrate exemplary views of the plate pad for the ostomy armor of FIG. 1.
Figure 6B:
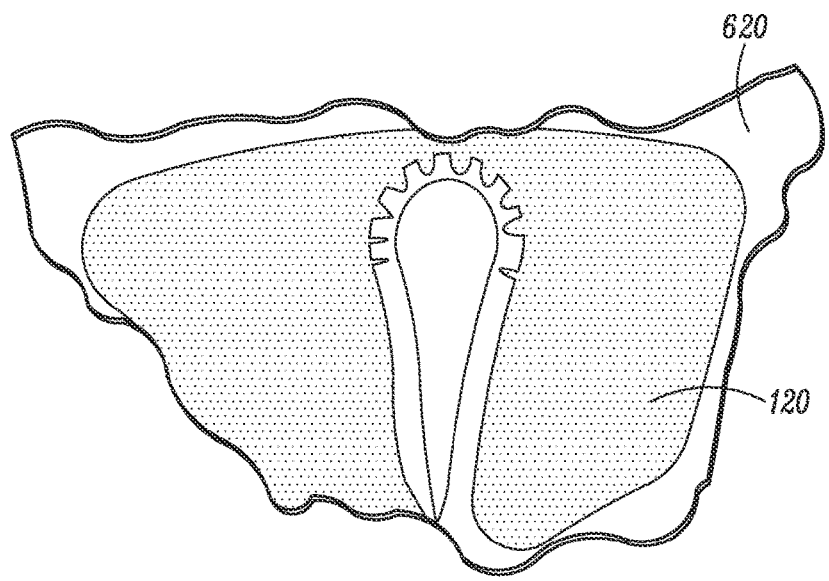

FIGS. 6A and 6B illustrate exemplary views of the plate pad for the ostomy armor of FIG. 1. According to an embodiment, plate pad 120 is made of soft material to be a comfortable and close-tolerance buffer between the base plate 110 and the wearer. Plate pad 120 is initially cut following the shape of mold 410. In an embodiment, the plate pad 120 includes a lower diagonal initial cut 601 in the relief channel, at which point the cut proceeds vertically for approximately 12.7 mm 602. Plate pad 120 further includes the 22.5 mm radius curve 604 at the apex of the relief channel. Parts 605, 606, and 607 of plate pad 120 consist the descending aspect of the relief channel. The relief channel is sized to allow most stomas at the upper aspect and widening as the channel continues toward the bottom or opening allowing waste pressure reduction from the stoma onwards into the holding bag. Plate pad 120 also includes the diagonal aspect of the pad 608 proximal to the leg. This diagonal cut 608 allows for a large range of motion for the wearer while preventing pinching of the ostomy armor 100 and the abdomen. Plate pad 120 also includes a horizontal aspect 609 of the pad. The horizontal aspect 609 allows for additional vertical range of motion. Plate pad 120 also includes the vertical medial aspect 610 proximal to the patient midline.

In another embodiment, plate pad 120 may be made/cut from a mold that is customized for fit to a particular wearer. For example, the customized mold may take into account certain unique body shape and characteristics of the wearer that is not in the generic plate pad mold 410, i.e., an obese person.

Plate pad 120 may be covered by plate pad cover 620 according to an embodiment. Plate pad cover 620 may be made from one or more of various material types, e.g., chamois, microfiber, terry cloth, cotton jersey knit, or any other material with similar properties. Plate pad 120 may be made from a porous material, e.g., ¼ inch, ⅜ inch, or ½ inch flexible closed or open cell foam with varying firmness, visco-elastic polymer, or any other material with similar properties.

An exemplary method of making the plate pad 120 according to an embodiment is as follows. Starting with suitable plate pad material, plate pad 120 is cut using a press 400 and a mold 410. The cut plate pad 120 may be covered by plate pad cover 620. Referring to FIG. 6B, plate pad cover 620 may be adhered on or coupled to plate pad 120 using glue or other means as known now or later derived. The plate pad cover 620 may only need to cover one side (the side facing the abdomen and not to be coupled to the base plate 110).

Figure 7A:
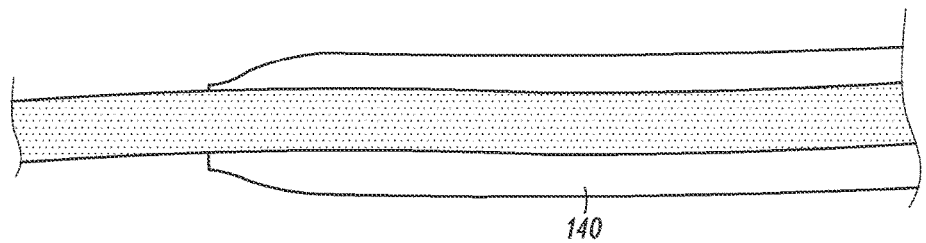
FIGS. 7A and 7B illustrate exemplary views of a waist pad for the ostomy armor of FIG. 1.
Figure 7B:
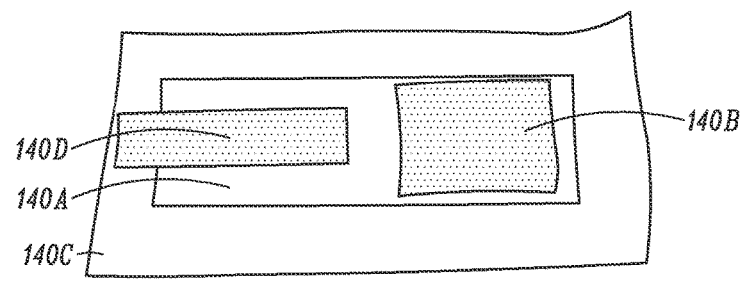

FIGS. 7A and 7B illustrate exemplary views of a waist pad for the ostomy armor of FIG. 1. In an embodiment, waist pad 140 is constructed using ⅛ inch thick foam 140A of either closed or open cell composition by widths that may vary from 1 inch to 4 inches or greater. Referring to FIG. 7B, 2 inch wide stiff webbing 140B provides a semi rigid backing to the foam 140A and chamois 140C or other appropriate material with similar properties, which are cut to an appropriate length, glued and pressed together to form the covering for the waist pad 140. Once cured, a 1 inch wide webbing 140D is cut to an appropriate length that extends beyond the foam 140A forming the waist pad 140 and is sewn to the backing.

In an embodiment, the materials of the waist pad 140, including foam 140A and chamois 140C, may be microfiber, terry cloth, cotton jersey knit, combinations of the same, and any other material with similar properties. The belt portion of waist pad 140, including webbings 140B and 140D, may be 1 inch and/or 2 inch MIL Spec nylon webbing, leather, cotton webbing, or any other material with non-elastic properties.

Once cured for about 30 seconds or more, a 1 inch wide webbing is cut to the appropriate length and sewn to the backing, with a 1 inch side-release tensioning buckle, to form the whole of the waist pad 140. Materials for the waist pad include ⅛ inch, ¼ inch, ⅜ inch flexible and firm closed or open cell foam, stiff nylon webbing of various widths.

In another embodiment, the foam 140A, a flexible closed cell foam with varying firmness, visco-elastic polymer, or any other material with similar properties is utilized to form the waist pad 140 including the belt. The belt portion is alternatively constructed using ⅛ inch foam, 2 inch wide webbing and chamois, or other appropriate material with similar properties, cut to the appropriate length, glued and pressed together. The backing of the waist pad 140 may be formed similarly as the belt.

Figure 8A:
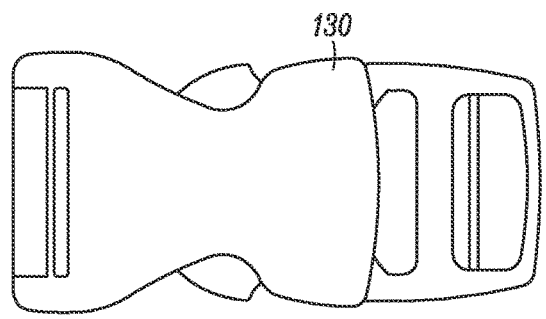
FIGS. 8A and 8B illustrate exemplary views of a buckle for the ostomy armor of FIG. 1.
Figure 8B:
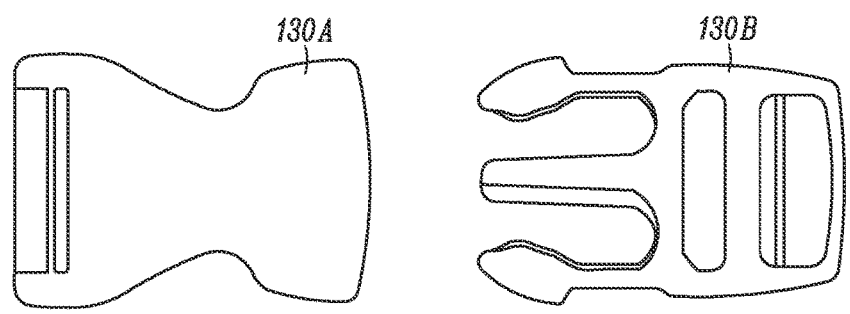

FIGS. 8A and 8B illustrate exemplary views of a buckle for the ostomy armor of FIG. 1. In an embodiment, buckle 130 is used as a connector. Buckle 130 includes a reception portion 130A and an insertion portion 130B, where when buckle 130 is closed, the insertion portion 130B is inserted into the reception portion 130A. Each non-connection ends of the insertion portion 130B and the reception portion 130A may be connected with 1 inch side-release webbing or other webbings corresponding with the extended webbing 140D of waist pad 140. The insertion portion 130B may also include a tensioning mechanism for the linch side-release webbing such that the webbing can be lengthened and shortened while looped and connected to the buckle 130, thereby providing a means of securing and comfortably tensioning the ostomy armor on the wearer.

The materials that make up the belt buckle 130 is 1 inch wide plastic side release tensioning, metal with finger, Mil-Spec hook and loop tape (Velcro™); a 2 inch wide plastic side release tensioning buckle may be used if the consumer is obese. In another embodiment, other coupling mechanisms may be utilized, e.g., clasp, and the like, or other materials may be used.

A method of making the ostomy armor 100 including base plate 110, waist pad 140, and buckle 130 according to an embodiment is as follows. Webbing 140D on one side of waist pad 140 is inserted into one of the slits 111, connecting the base plate 110 with the waist pad 140. The webbing 140D on the other side of waist pad 140 is inserted into the insertion portion 130B of the buckle 130. A piece of webbing similar to webbing 140D connects the reception portion 130A with the other one of the slits 111. In one embodiment, the belt portion of ostomy armor 100 includes the waist pad 140, the buckle 130 and the associated webbings 140D.

A method of wearing the ostomy armor 100 according to an embodiment is as follows. The connected ostomy armor 100 is unlocked at the two portions of the buckle 130. The wearer places the base plate 110 on the stoma, with the plate pad 120 covering and supporting the stoma, and the base plate 110 faces outward away from the body to provide rigid protection against outside objects. The waist pad portion is swung around to the back of the body providing comfort and support. As such, the ostomy armor 100 loops around the body and may be locked in the front of the body by connecting the two portions of buckle 130. As discussed above, the webbing is configured to go through the slits of the plate to provide a way to tighten the plate around the user. In addition, the webbing is sized and variably adjustable to allow a user to set the length and use over and over again with simply the buckle.

Figure 9A:
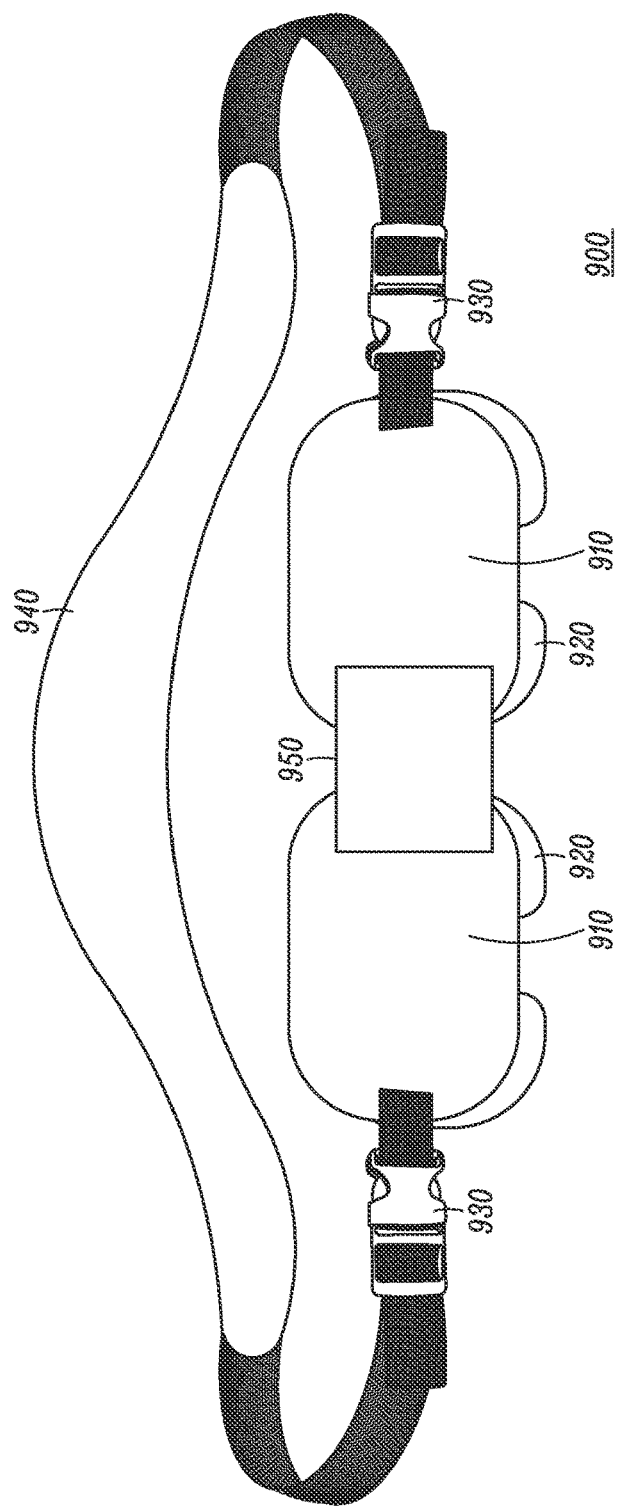

FIGS. 9A, 9B, and 9C illustrate exemplary views of a dual ostomy armor according to an embodiment. Dual Ostomy armor 900 includes dual base plates 910 and plate pads 920, webbing 950 connecting the dual base plates 910, dual connectors 930, and waist pad 940. The dual ostomy armor 900 is similar to the ostomy armor 100 discussed above with respect to FIGS. 1-8. The dual ostomy armor 900 includes two base plates 910 and plate pads 920 for protecting two stoma of the wearer. For example, an application of dual ostomy armor 900 includes where the wearer has one stoma for waste and another stoma for a feeding tube.

The construction for the base plates 910 is similar to the base plate 110 as disclosed above with respect to FIG. 2-4. The construction of the plate pads 920 is similar to the plate pad 120 as disclosed above with respect to FIGS. 5-6. The constructions of the waist pad 940 and the connectors 930 are similar to the waist pad 140 and the connector 130 as disclosed above with respect to FIGS. 7-8.

In another embodiment, the construction of the base plates 910 may include creating slits and of varying sizes to accommodate the different sizes of webbings used, i.e., webbing 950 connecting the two base plates 910 is a larger size than webbings 940D connecting each base plate 910 to the buckles 930. Webbing 950 may be made of the same material as webbings 940D or may be of another suitable material. In a further embodiment, base plates 910 may be created of varying sizes, i.e. one base plate may be larger than the other as one may be configured to be placed over a stoma for waste (which may include a waste bag) and the other is for a feeding tube. Also, both base plates 910 may be of a comparatively different size than the base plate 110 of the single ostomy armor 100, i.e., base plates 910 may be smaller than base plate 110 for a comparatively sized person.

A method of making the dual ostomy armor 900 including base plates 910, waist pads 940, and buckles 930 according to an embodiment is as follows. Webbing 950 connects the two base plates 910 through slits. A piece of webbing connects the other slit on each side of waist pads 940 to a respective buckle 930. Each side of the waist pad 940 is connected to one of the two buckles 930. As such, the loop of dual ostomy armor 900 forms a completed belt.

Further referring to FIG. 9A, the two outside buckles 930 correspond to the center of pull for the adjustable waist pad while the two center adjustment points (i.e., webbing 950) show a slight vertical offset. This allows for the patient to adjust the separation between the two base plates 910 in the x-axis and also adjustment in the y-axis to compensate for weight gain, loss, and growth of the patient. In one embodiment, the attachment mechanism between the plates is a hook and loop fastener system, e.g., Mil-Spec grade 2 Velcro™.

Figure 10:
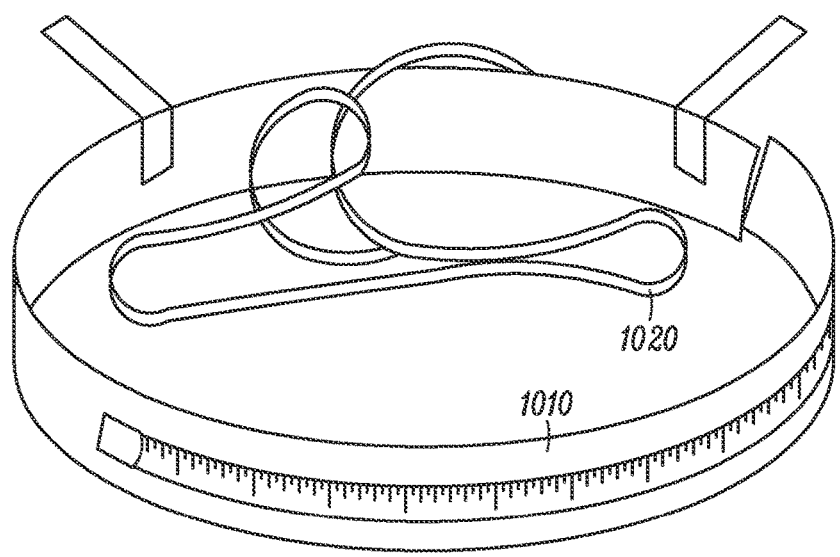
FIG. 10 illustrates a plotting and assembly tool for an ostomy armor according to an embodiment.

FIG. 10 illustrates a plotting and assembly tool for an ostomy armor according to an embodiment. Dual ostomy armor 900 includes the fitting of two base plates over two separate stoma of variable distances apart. As such, it is desirable that the dual ostomy armor 900 be of custom fit for the wearer to ensure that the two base plates fit over the wearer's two stoma.

Plotting and assembly fixture includes horizontal measurement tape 1010 and vertical measurement tape 1020. Plotting and assembly fixture may be made of plastic, metal, or other suitable materials and is shaped to follow the curve of the human body, i.e., the abdomen. The horizontal measurement tape 1010 is fixed on and follows the curve of the fixture, with the measurement size of the measurement tape 1010 centered on a midline marking on the fixture.

A method of using the plotting and assembly fixture according to an embodiment is as follows. The fixture is fitted on the wearer's body with the curve of the fixture following the curve of the body of the wearer. The midline marking on the fixture is aligned midline of the wearer, i.e., the vertical center line of the wearer. The fixture is moved vertically on the body of the wearer such that the two stoma to be fitted are visible. The horizontal measurement tape 1010 is used to measure the horizontal offset of the two stomas versus each other and versus the midline. The vertical measurement tape 1020 is used to measure the vertical offset of the two stomas and a default position, i.e., a desirable position in the abdomen most suitable for wearing the belt of the dual ostomy armor 900.

From the horizontal and vertical offsets measured, dual ostomy armor 900 may be custom made for the wearer. For example, slits may be custom cut to various length and angles to accommodate different stoma locations, i.e., one stoma may be vertically higher up on the body than the other stoma, as such, the two base plates 910 may be positioned through angled slits such that a base plate 910 is vertically higher than the other to be positioned naturally over the two stoma. In another example, base plates 910 may be cut and shaped to correspond to shape and offset for the two stoma. In yet another example, the adjustment may be made at the adjustment points of the buckles 930 or the webbing and center adjustment point 950.

In another embodiment, the custom measure of the wearer's body may be performed using other means as now known or later derived, e.g., using a 3D scanner.

Figure 11:
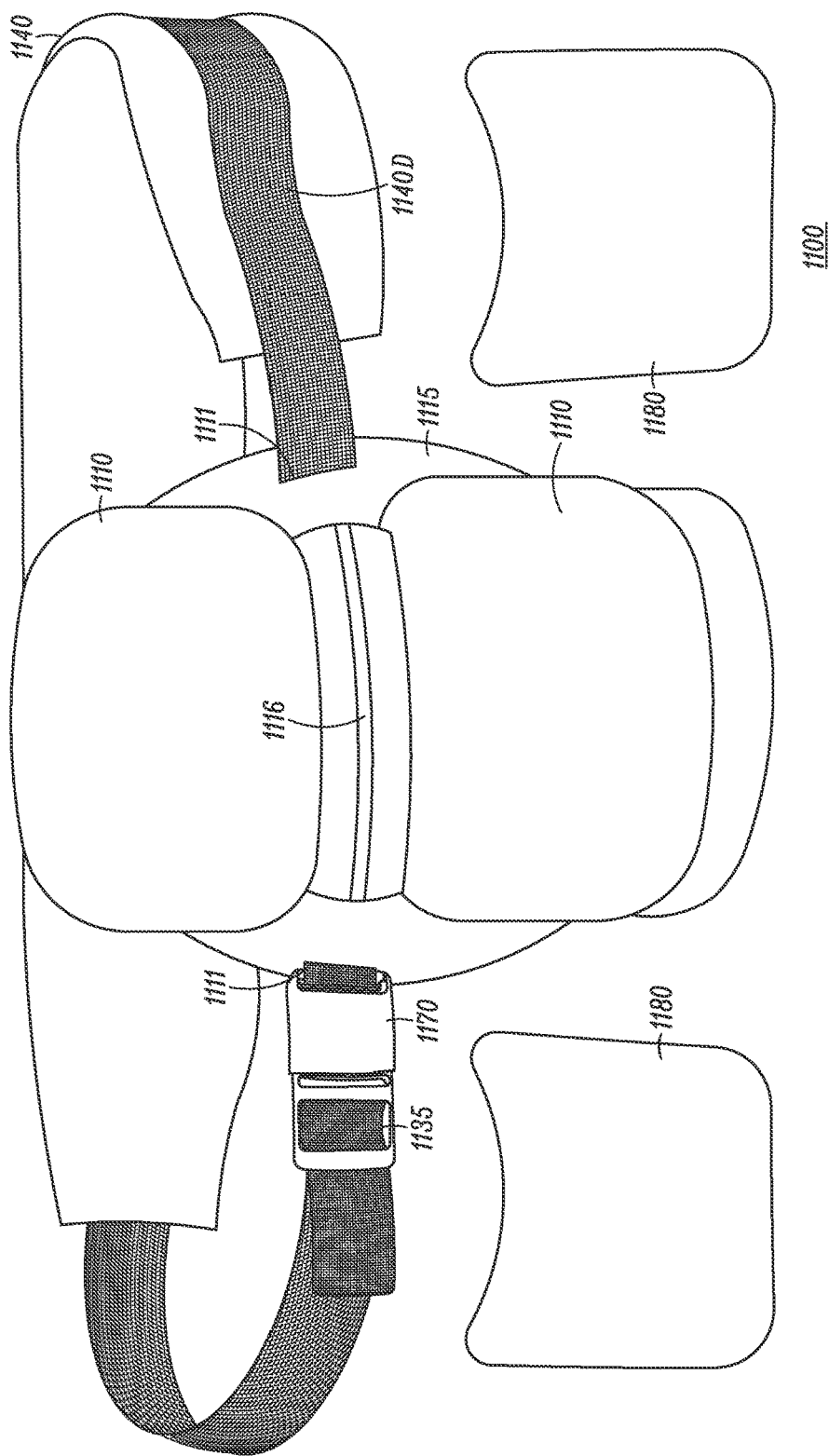
FIG. 11 illustrates a vertical dual ostomy armor according to an embodiment.

FIG. 11 illustrates a vertical dual ostomy armor according to an embodiment. Vertical dual ostomy armor 1100 includes vertical base plates 1110, plate pad 1115, base plates connector 1116, buckle 1135, waist pad 1140, belt pad 1170, and waste bag armors 1180. The vertical dual ostomy armor 1100 may be used to protect two stoma aligned substantially vertically from one another.

In one embodiment, the construction of the various component of vertical dual ostomy armor 1100 is similar to the ostomy armor 100 as disclosed with respect FIGS. 1-8 and ostomy armor 900 as disclosed with respect to FIGS. 9A-9C. For example the construction of waist pad 1140 is similar to the construction of waist pad 140 as disclosed with respect to FIGS. 7A-7B.

In another embodiment, construction of the vertical dual ostomy armor 1100 includes some differences from ostomy armor 100 and dual ostomy armor 900. Base plates 1110 are positioned to be vertically aligned. As such, base plates 1110 may be constructed such that the shape follow the shape of the abdomen vertically. In one embodiment, the back of base plates 1110 may be supported by a single plate pad 1115 covering the area of both base plates 1110 the accommodate the connection with the belt and waist pad 1140. As such, slits 1111 may be cut from the sides of the plate pad 1115, unlike slits 111 in the base plate 110 for the ostomy armor 100. The vertically aligned base plates 1110 may be connected using a webbing 1116 or other suitable materials.

The vertical ostomy armor 1100 may be connected using a belt to waist pad 1140 similar to the ostomy armor 100. Vertical ostomy armor 1100 may include buckle 1135, which is a tensioning buckle 1135 without two portions connectors of buckle. In another embodiment, the various ostomy armors use various buckles as disclosed herein or other types as known now or later derived.

Vertical ostomy armor 1100 further includes a belt pad 1170. Belt pad 1170 provides further comfort and protection to the front of the wearer's body when the belt is tightened similar to waist pad 1140. Belt pad 1170 may be constructed in a similar process as with waist pad 1140, using similar composition and materials. For example, materials of belt pad 1170 may be chamois, microfiber, terry cloth, cotton jersey knit, combination of the same or any other material with similar properties. Belt pad 1170 may also include a backing similar to waist pad 1140 which includes 1 inch and/or 2 inch MIL spec nylon webbing, leather, cotton webbing, combination of the same, and any other material with non-elastic properties. Belt pad 1170 may be positioned close to the armor plate portion 1110 on the belt of the ostomy armor 1100 to protect the user from the pressure from the tightening of the belt because the vertical base plates 1110 are of a relatively larger size. In other embodiments, other ostomy armor may also include a belt pad.

Protection devices 1180 may also be used with vertical ostomy armor 1100 and is described with references to FIG. 15-16 below.

Figure 12:
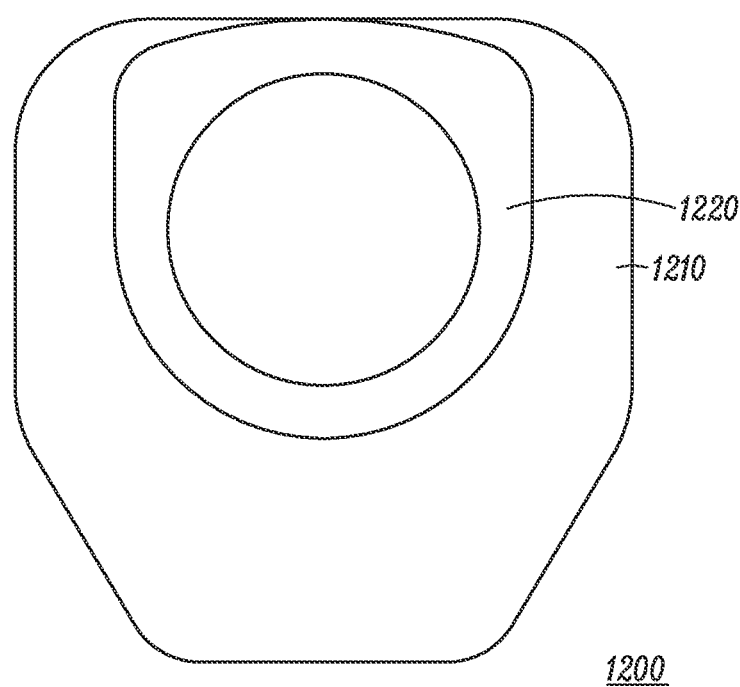
FIG. 12 illustrates an exemplary view of a waste wick assembly according to an embodiment.

FIG. 12 illustrates an exemplary view of a waste wick assembly according to an embodiment. Waste wick includes waste wick material portion 1210 and a tape portion 1220. Waste wick material portion 1210 may be made from highly absorbent materials such as cellulose or any fibrous material that has highly absorbent material properties. In another embodiment, a barrier material, e.g., plastic, may be optionally added to one side of the absorbent material. The barrier material will provide other enhanced protection against bleed through of matters absorbed by the waste wick material 1210.

In one embodiment, the tape portion 1220 is optional. The tape portion may be double sided tape and made from a high/low tack acetate, a porous paper double sided tape, or other materials with similar tack properties. One side of the tape portion 1220 sticks onto the waste wick material 1210. The other side of the tape portion 1220 is left unused until the waste wick 1200 is ready to be deployed to a waste collection bag.

Figure 13A:
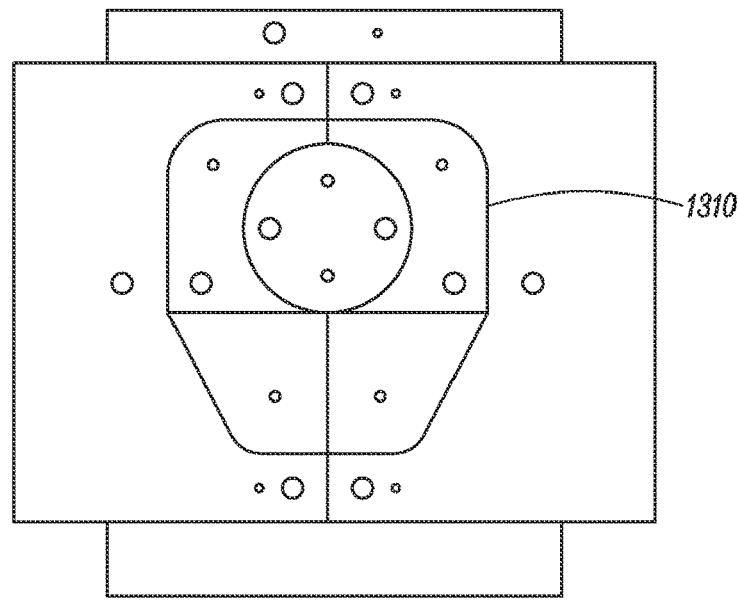
FIGS. 13A and 13B illustrate exemplary views of an apparatus for cutting the waste wick assembly of FIG. 12.
Figure 13B:
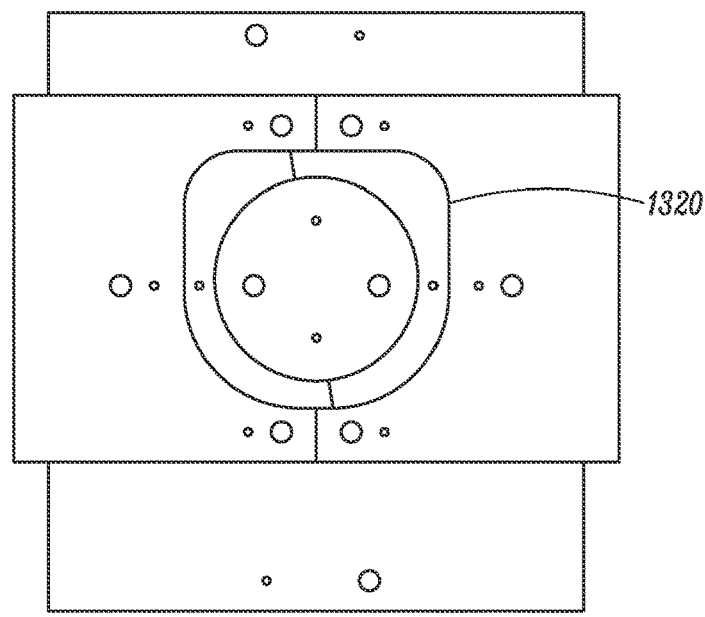

FIGS. 13A and 13B illustrate exemplary views of an apparatus for cutting the waste wick assembly of FIG. 12. Cutting apparatus includes a waste wick material portion cutting die 1310 for cutting the waste wick material into a predetermined geometry suitable for the application of the waste wick 1200. As such, the geometry of the cutting die 1310 is configured to maximize the collection of any waste material that may leak from a waste collection device. The geometry of the circular hole of the cutting die 1310 (and hence the resulting waste wick material portion 1210) relates to and is dependent on the flange the waste collection bag. The tape portion cutting die 1320 is used to produce the optional double sided tape portion.

A method of making a waste wick 1200 using the cutting apparatus 1300 according to an embodiment is as follows. A material suitable to be the waste wick portion 1210 is placed on the cutting apparatus and is cut to the waste wick geometry using the waste wick cutting die 1310. A material suitable to be the tape portion 1220 is placed on the cutting apparatus and is cut to the tape portion geometry using the tape portion cutting die 1320. The resulting tape portion 1220 can be taped to the waste wick portion 1210 to produce the waste wick 1200. The cutting apparatus as exemplified in an embodiment can be disassembled in order to replace the cutting blades and the cutting die, such as replacing the cutting dies 1310 and 1320. Additionally, the configuration of the blades can be changed to cut a different shape of waste wicks.

Figure 14A:
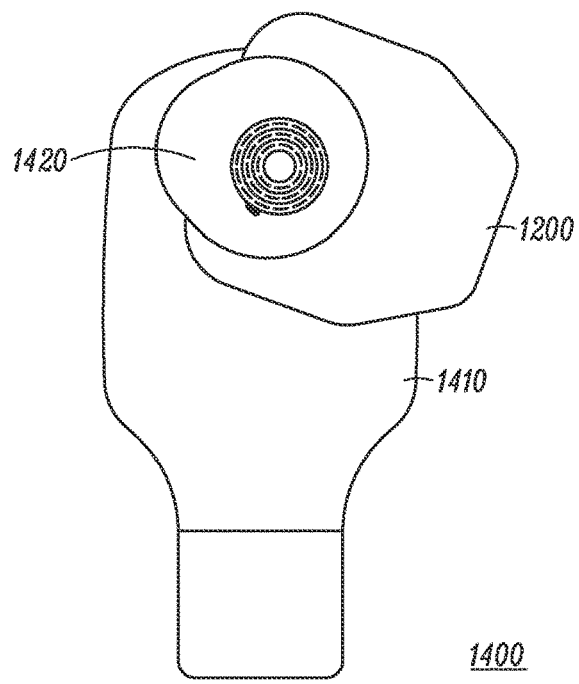
FIGS. 14A and 14B illustrate exemplary views of an ostomy appliance including a waste collection bag and a waste wick according to an embodiment.
Figure 14B:
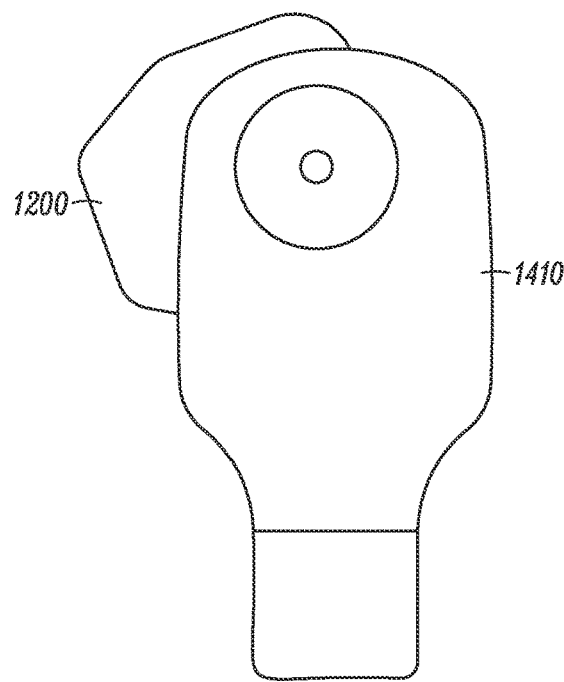

FIGS. 14A and 14B illustrate exemplary views of an ostomy appliance including a waste collection bag and a waste wick according to an embodiment.

One issue with a waste collection bag for an ostomy site is that the waste collection bag may unavoidably leak due to various reasons, i.e., damage, puncture, or latent defects to the waste collection bag or careless handling during wear and at removal. Accordingly, waste wick 1200 serves as a protective and absorbent layer system to mitigate the propagation of exposed liquid and semi-solid waste. Waste wick 1200 further mitigates waste exposure due to the incomplete connection between the ostomy and the waste collection bag.

A method of using the waste wick 1200 according to an embodiment is as follows. Waste collection bag 1400 includes a waste bag portion 1410 and a flange 1420. The flange 1420 surrounds the skin barrier tube where the waste collection bag 1400 connects with the ostomy site to collect the waste from the body of the wearer. The flange 1420 may be made of absorbing materials to seal and absorb any spillage at the site of the ostomy connection with the waste collection bag. Waste wick 1200 may be placed behind the flange 1420 and in position to absorb leaks from the bag portion 1410. The optional tape portion 1220 of waste wick 1200 may be stuck to either the back of the flange 1420 or the bag portion 1410 of the waste collection bag 1400 to further secure the waste wick 1200 to the waste collection bag 1400. It is noted that an edge of an ostomy collection bag may be susceptible to working loose from the users abdominal wall and allowing human waste a pathway to exposure. Waste wick 1200 is in a position to absorb any leaking waste from a separation of the waste collection bag 1400 and the abdominal wall.

In one embodiment, the absorbent material is dimensioned to substantially conform to a dimension of the waste bag. In another embodiment, waste wick 1200 may also be used in conjunction with any bag and barrier combination system presently in production.

Figure 15:
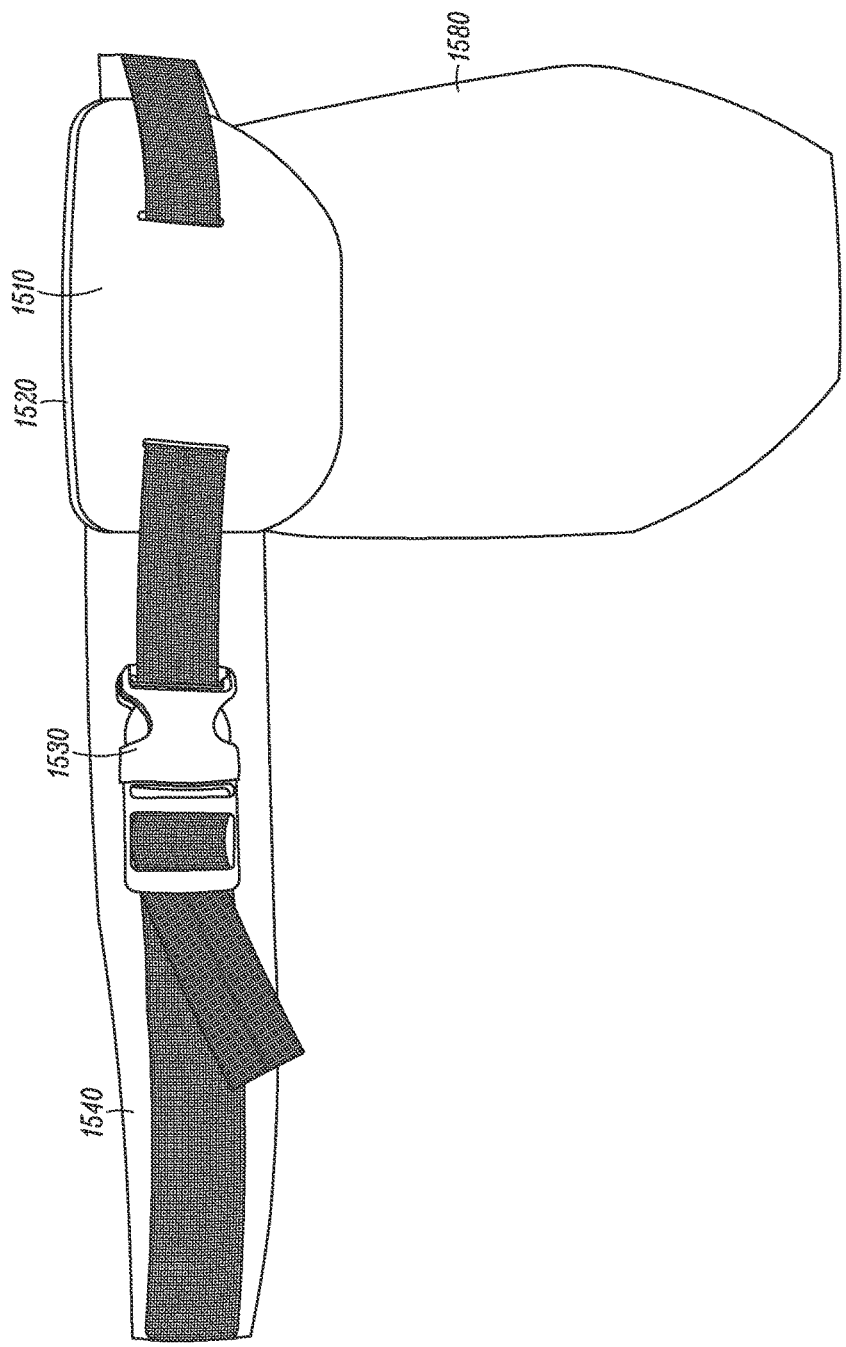
FIG. 15 illustrates an exemplary view of an ostomy armor and armor bag face according to an embodiment.

FIG. 15 illustrates an exemplary view of an ostomy armor and armor bag face according to an embodiment. Ostomy armor is similar to ostomy armor 100. Ostomy armor includes a base plate 1510, a plate pad 1520, a buckle 1530, and a waist pad 1540. Ostomy armor may include an armor bag face 1580.

As discussed above, a waste collection bag is prone to leaks, cuts, tears, and other damages that may occur due to the frail nature of the waste collection bag. An person with an ostomy may remain active after major surgery, though in a more careful manner, as their ostomy system, including the waste collection system are vulnerable to the motions, actions and physically hostile work environments. Punctures or tears in the waste collection bag throughout a work day, during school, or in recreation can result in hazardous biomedical waste contaminating the immediate area. The inclusion of the armor bag face 1580 to an ostomy armor mitigates the chances of such damages to the waste collection bag by providing rigid protection to the waste collection bag. The armor bag face 1580 further facilitates comfort and maintenance of wearing the system and may work with other ostomy armors, such as dual ostomy armor 900 or the vertical ostomy armor 1100 (e.g., armor bag face 1180), according to further embodiments.

Figure 16A:
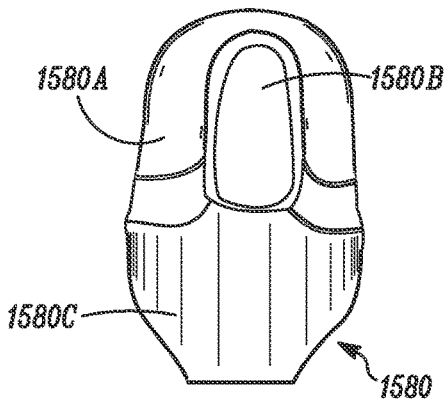
FIGS. 16A, 16B, 16C, and 16D illustrate exemplary views of the armor bag face of FIG. 15.
Figure 16B:
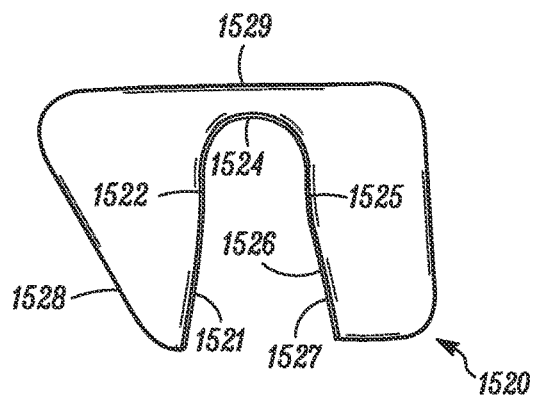
Figure 16C:
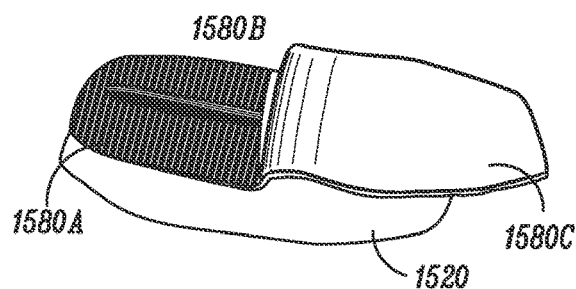
Figure 16D:
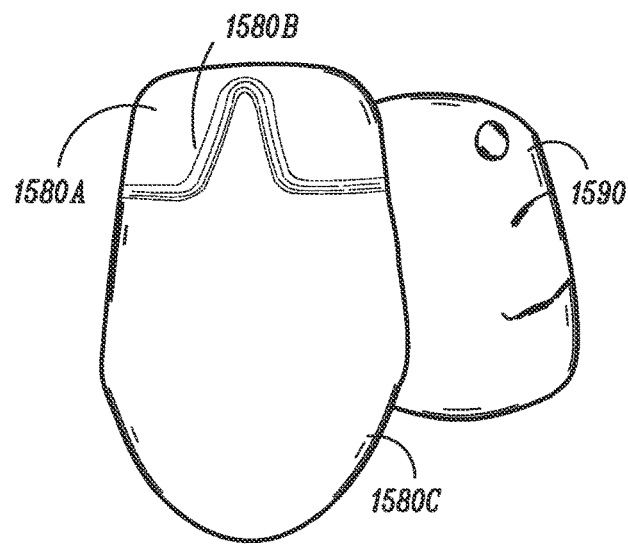

FIGS. 16A, 16B, 16C, and 16D illustrate exemplary views of the armor bag face of FIG. 15. Referring to FIG. 16A, the front side (the side facing away from body of the wearer) of armor bag face 1580 is shown. Referring to FIG. 16B, a plate pad 1520 is shown, where the plate pad 1520 is coupled to and fills the back side (the side facing toward the body of the wearer) of armor bag face 1580 is shown. Referring to FIG. 16C, a side of the armor bag face 1580 is shown. Referring to FIG. 16D, a back side of the armor bag face 1580 (without the plate pad 1520) in shown in relation to a waste collection bag 1590.

The armor bag face 1580 is configured to cover a waste collection bag 1590 used with an ostomy or stoma, thereby providing enhanced protection of an impact. In a preferred embodiment, the protection device has an outside geometry to cover at least the lower portion of the waste bag 1590. According to an embodiment, armor bag face includes a side plate 1580A, a raised channel 1580B, and a protective area 1580C.

The armor bag face 1580 may be constructed from any rigid material, e.g., fiberglass, nylon, injection molded fiberglass, reinforced ABS, thermoplastics, and/or high performance plastics, e.g., Kydex™. In a preferred embodiment, the protective device is formed from carbon fiber material. In another embodiment, the armor bag face 1580 may be constructed by similar materials and methods as ostomy armor 100.

In an embodiment, the armor bag face 1580 includes a three-dimensional geometry configured to work with an ostomy armor, such as ostomy armor 100, dual ostomy armor 900, or vertical dual ostomy armor 1100 (vertical dual ostomy armor 1100 is illustrated to include two armor bag faces 1180 in the exemplary embodiment). In this embodiment, the front and reverse aspects on the upper half of the device utilizes a raised channel 1580B matching the cutout of the plate pad 1520, as defined by parts 1521, 1522, 1524, 1525, 1526, 1527, 1528, and 1529 of plate pad 1520. The various parts 1521, 1522, 1524, 1525, 1526, 1527, 1528, and 1529 of plate pad 1520 is similar to the plate pad 120 as disclosed with respect to FIG. 6 above. The raised channel 1580B is intended to reside within the afore mentioned cutout of plate pad 1520 as defined by parts 1521, 1522, 1524, 1525, 1526, and 1527. The side plate 1580A provides accommodation to the plate pad 1520 for coupling of the parts defined by 1528 and 1529 to the armor bag face 1580. The protective area 1580C, e.g., three-dimensional area, accommodates, covers, and provides an external protective barrier to the waste collection bag 1590 whether full, partially full, or not full.

Referring to FIG. 16C, in an embodiment, the protective area 1580C of armor bag face 1580 is flexible, e.g., a flexible laminate made up from ballistic nylon, Kevlar™, and chamois, while the upper portions 1580A and 1580B is constructed of composite rigid material described herein. The back side of the armored bag face 1580 may be constructed of soft material.

Figure 17:
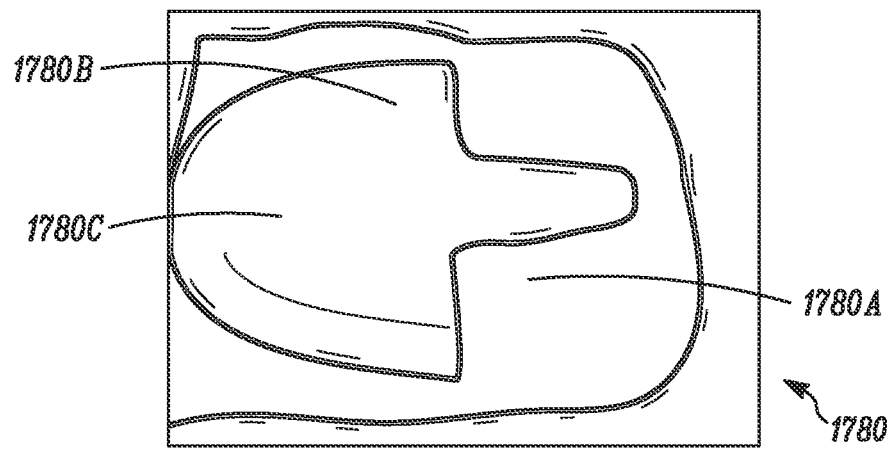
FIG. 17 illustrates an exemplary view of a mold for the armor bag face of FIG. 15.

FIG. 17 illustrates an exemplary view of a mold for the armor bag face of FIG. 15. Three-dimensional mold 1780 is used in the vacuum molding process to form the armor bag face 1580 according to an embodiment. In this embodiment, the mold 1780 is shown on its side with the top proximal to FIG. 17. The mold 1780 includes a region 1780A (corresponding to the side plate 1580A of the armor bag face 1580) having a radius, e.g., 9 inch radius, that approximates the left to right curve of an average lower abdominal quadrant.

Region 1780B is a recessed portion of mold 1780 A and corresponds to the raised channel 1580B of the armor bag face 1580. The recessed region 1780B ceases and the bump out to region 1780C, which corresponds to the protective area 1580C, begins.

During a vacuum molding process for making an armor bag face 1580 using the mold 1780 according to an embodiment, no epoxy is applied to region 1780C. As a result, the resulting protective area 1580C from the region 1780C remains flexible.

A method of molding the armor bag face 1580 using the mold 1780 according to an embodiment is as follows. The facility in which the molding process is taking place is clean and all of the materials temperature stabilized to between 75 and 80 degrees. A vacuum pressure gauge is installed to a section of flexible hose approximately 12 inches long, and the open end of the hose is placed on to the sealing tape so the end remains inside of the bagging film during the curing process. This will enable the production person to monitor vacuum pressure during the molding process. The vacuum is used once the appropriate materials are layered on the mold to shape the materials to the shape of the mold.

Armor bag face 1580 can be constructed of a number of materials, e.g., carbon fiber, injected molded laminate of Kevlar™ and polystyrene, polypropylene, Kydex™, nylon, combination of the same, or any other material with similar properties. In one embodiment, the first layer of the upper half of the mold is carbon fiber followed by a thin layer of epoxy resin and then a layer of Kevlar™, another thin layer of resin, followed by a final layer of carbon fiber. The lower portion center layer of Kevlar™ left dry; to that, on the front face lower half, one layer of heavy grade, ballistic nylon, or a similar material may be applied.

Figure 18:
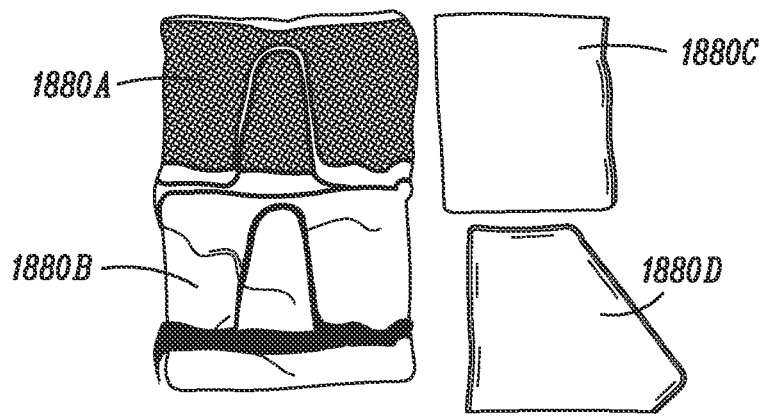
FIG. 18 illustrates an exemplary composite view of the armor bag face of FIG. 15.

FIG. 18 illustrates an exemplary composite view of the armor bag face of FIG. 15. Referring to FIG. 18, a composite view of an exemplary armor bag face 1580 after formed and removed from the mold is illustrated showing the various layers of materials. After being formed, the armor bag face 1580 is removed from the mold. The upper portion 1880A corresponds to a relief of region 1780A of mold 1780 (corresponding to the side plate 1580A and the raised channel 1580B of the armor bag face 1580). The lower portion 1880B corresponds to region 1780C of the mold 1780 (corresponding to the protective area 1580C of the armor bag face 1580). In this embodiment, the upper portion 1780A is non-flexible, e.g., rigid, and lower portion 1780B is flexible.

Part 1880C, corresponding to the front of part 1880B, illustrates an example of ballistic nylon used in covering the lower front Kevlar™ portion of the protective area 1580C. The bonding of heavy duty ballistic nylon to the forward side of the Kevlar™ face prevents sharp punctures as a first measure of defense. The Kevlar™ as shown in FIG. 1880B (on the back of ballistic nylon part 1880C) serves as the defense against cuts and tears. Part 1880D illustrates the chamois leather which fully covers the entire reverse of the armored bag face 1580 and is bonded to the structure using common contact cement. The completed assembly features a hard or non-flexible upper portion with the entire lower bonded portion remaining flexible through all ranges of motion.

In a preferred embodiment, the materials used for the composition of the armor bag face as shown in FIG. 18 is as follows. The materials include 1880A Carbon fiber, 1880B Kevlar™, 1880C ballistic nylon and 1880D Chamois leather. In another embodiment, other materials may also be used. The protective barrier 1880C may be formed with other techniques and materials. For example, it may be formed with plastic molding, thermoplastics, metal pressure molding, and the like. In other embodiments, the armor bag face 1580 may be formed using other techniques as now known or may be later derived.

In making the ostomy armor according to an embodiment, the base plate 1510 is assembled with the armor bag face 1580 to cover the upper portion 1580A (including the raised channel 1580B). As such, only the protective cover 1580C, which is either rigid or non-rigid, would be exposed to face the outside of the wearer's body. In an embodiment, as plate pad 1520 is coupled to 1580A instead of directly to base plate 1510, this assembly is different from ostomy armor 100 and the like which has plate pad 120 coupled directly to base plate 110.

Figure 19A:
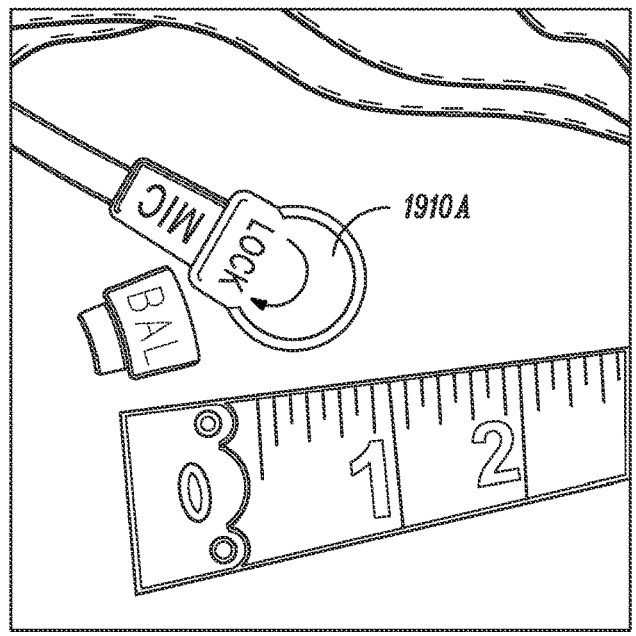
FIGS. 19A and 19B illustrate exemplary views of unprotected feeding tube stomal system.
Figure 19B:
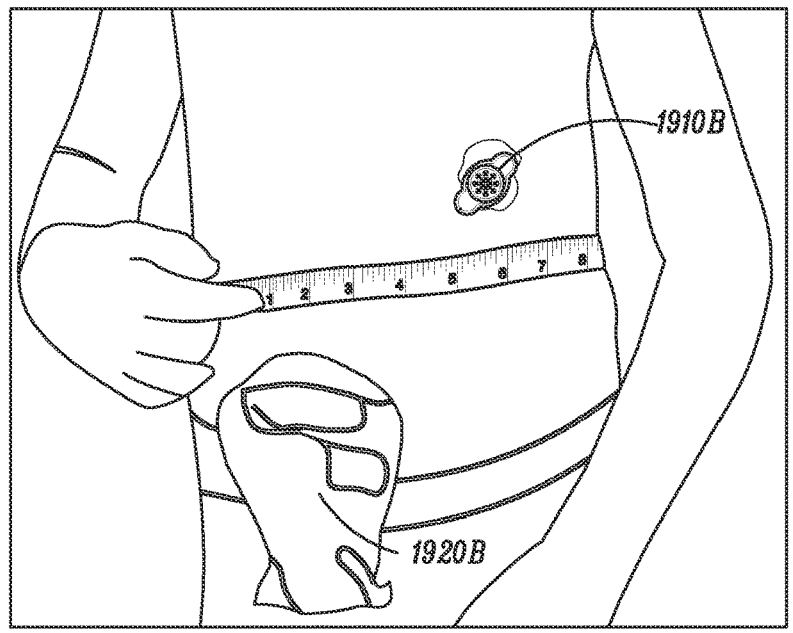

FIGS. 19A and 19B illustrate exemplary views of unprotected feeding tube stomal systems according to embodiments. Feedings tubes 1910A and 1910B are two of a number of types of unprotected feeding tubes. Referring to FIG. 19A, feeding tube 1910A is an example of one type of a feeding tube device. Feeding tube 1910A contains a lock feature, which enables the care giver to replace the tube portion of the device without disturbing the hub. This feature will be discussed in subsequent paragraphs below. Referring to FIG. 19B, FIG. 19B illustrates feeding tube 1910B and stoma (with a waste collection bag) 1920B on the same person. The two devices 1910B and 1920B have an offset at both the x-axis and y-axis between the two devices. The offset will be discussed in the subsequent paragraphs below. The feeding tube 1910B induced skin irritation on the wearer. It is also noted that both feeding tubes 1910A and 1910B protrude from the patients abdominal wall approximately 0.75 inch or less.

As such, the unprotected feeding tubes are highly susceptible to external trauma as well as the risk to the patient. Deficiencies with the unprotected feeding tubes include that, through normal use, play, and other various normal activities, the wound site tends to become distended and elongated leading to an increased possibility of infection and improper fitting of the stomal site to the feeding tube apparatus. As such, it is desirable for a feeding tube protection system that is able to prevent herniations, leaks, and elongated incision sites, and to make the protection system resilient against impact damages. It is further desirable for the protection system to conform to the abdominal region and be able to work with an ostomy armor system to facilitate protection, comfort, and maintenance of wearing the one or more parts of the system.

Figure 20:
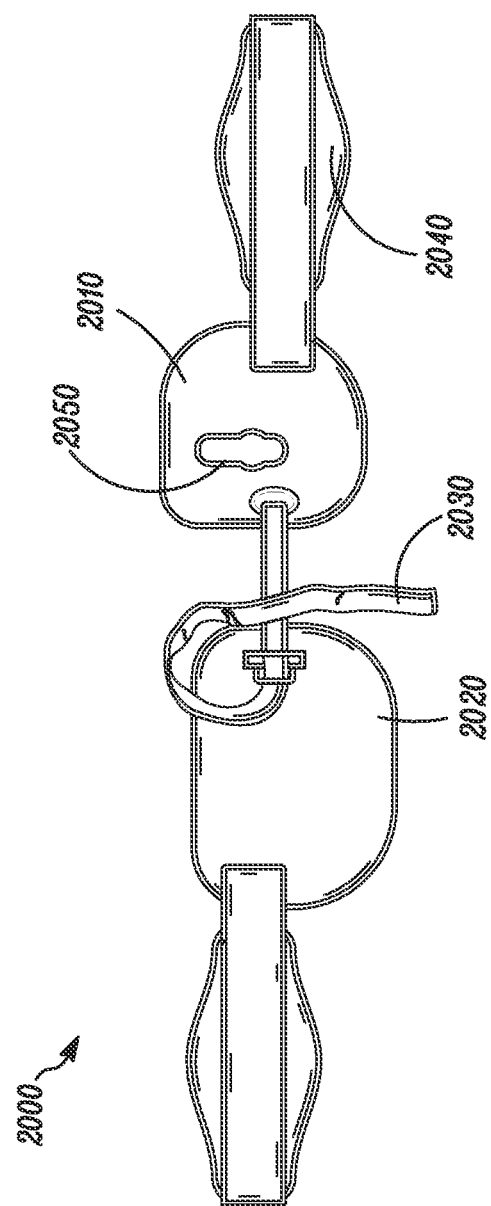
FIG. 20 illustrates an exemplary view of a protection system for feeding tubes according to an embodiment.

FIG. 20 illustrates an exemplary view of a protection system for feeding tubes according to an embodiment. Protection system 2000 includes a feeding tube armor 2010 and an ostomy armor 2020. Protection system 2000 further includes buckle 2030 for connecting the feeding tube armor 2010 and the ostomy armor 2020. Protection system 2000 also includes belt 2040 to facilitate the wearer in wearing the protection system 2000.

In an embodiment, the protection system 2000 may be single consisting of only the feeding tube armor 2010 or may be dual consisting of both the feeding tube armor 2010 and the stoma armor 2020. The feeding tube armor 2010 is built for stabilization and protection of the stoma site and/or feeding tube site without restriction of flow, by granting a loose-tolerance fitting for a feeding tube locking mechanism and a channel to clamp the catheter tube in place. More specifically, the window in the plate is shaped to allow the care giver to visually check to insure that the feeding tube and hub are locked as well as check nutrient flow. Following the window up or down from the reverse of the plate allows the feeding tube itself to exit from the top or bottom according to the patient's and/or care giver's preference.

It is noted that the viewing window 2050 which allows the care giver to rapidly access the lock and security of the tube hub. The channel is formed by a vertical separation of the plate pad at the tube site of the protective system allowing the tube to egress out of the top or bottom of the feeding tube armor 2010.

In a preferred embodiment, a quick disconnect adjustment strap and vertical offset 2030 may be utilized. This allows for the patients tube site and stoma to be protected as the body changes due to weight loss and gain and growth. Optionally, a hook and loop, e.g., Velcro™ may be used to fasten the feeding tube armor 2010 with the stoma armor 2020. In one embodiment the stoma armor includes an embodiment of the ostomy armor 100, 900, or 1100 as disclosed above.

Figure 21A:
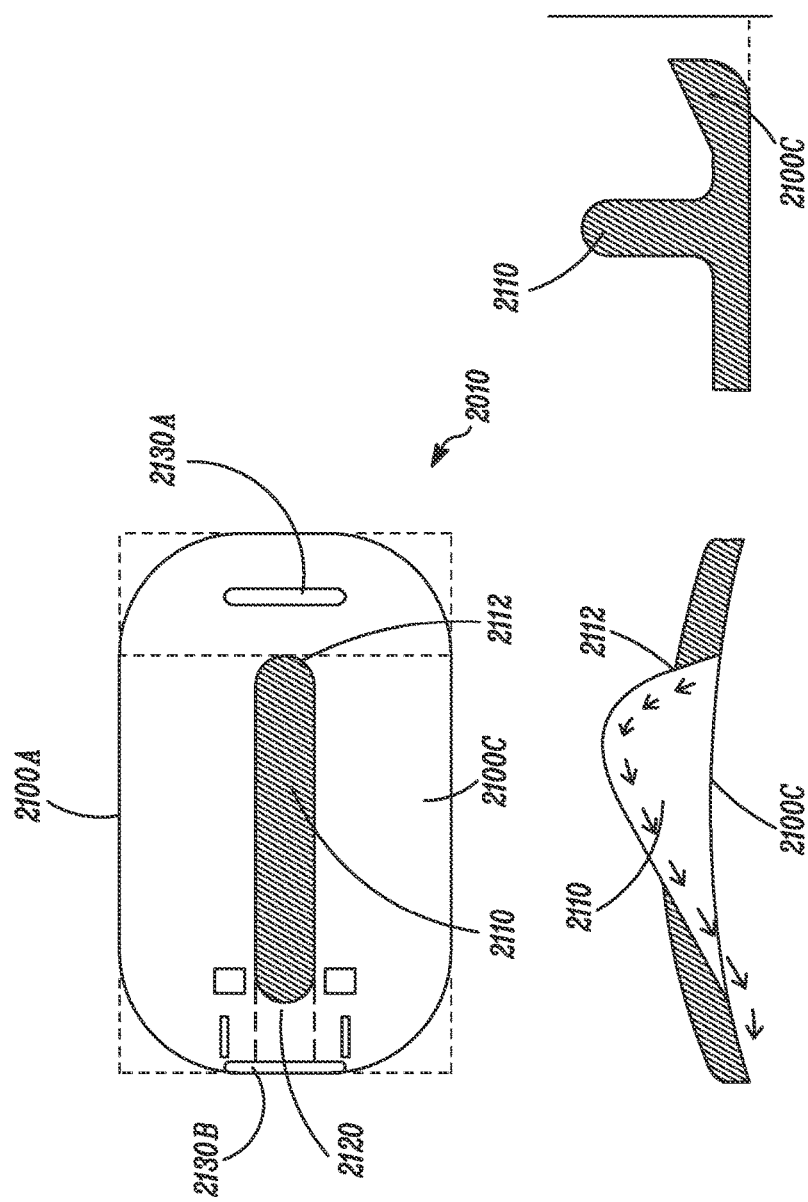
FIGS. 21A and 21B illustrate exemplary views of the feeding tube armor of FIG. 20.
Figure 21B:
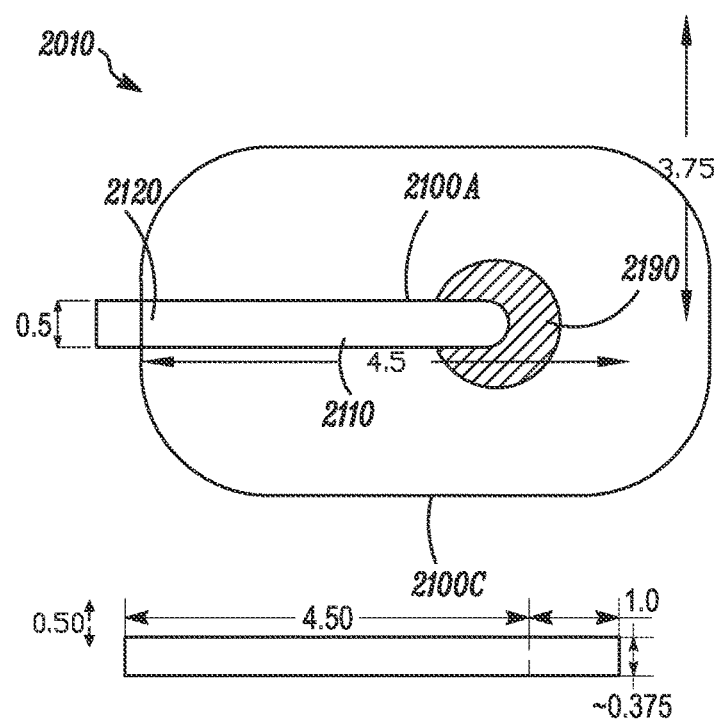

FIGS. 21A and 21B illustrate exemplary views of the feeding tube armor of FIG. 20. Feeding tube armor 2010 includes a top portion 2100A and a bottom portion 2100C defining the overall shape of the feeding tube armor 2010 and allowing for load distribution. Feeding tube armor 2010 also includes a recessed portion 2110 that allows the insertion of the feeding tube to the feeding tube armor 2010 and guides the feeding tube along a protected pathway from the infusion site to the nutrient source. The head 2112 of the recessed portion 2110 directly faces the hub where the feeding tube comes outside of the wearer's body. The head 2112 applies a light pressure to the feeding tube hub, thereby preventing the elongation of the infusion site and preventing the feeding tube from being pulled from the patient, e.g., preventing the feeding tube from being snagged or pulled in an unwanted fashion.

Referring to side views of feeding tube armor 2010 with reference to FIG. 21A, the bottom portion 2100C of the feeding tube armor 2010 is not only curved to approximate the average upper abdominal curvature but also pushed out to provide additional range of motion.

Slit 2130A is a 1 inch by ⅛ inch slit used for securing the retention belt 2040 to the feeding tube armor 2010. Slit 2130B is for securing the tube relief and tensioning buckle 2030 to the stoma armor 2020. In an embodiment, the axis of the slit 2130A is directly along the line of pull or in the same plane as the tube relief and tensioning buckle 2130B. In another embodiment, slits 2130A and 2130B may be customized at various angles on feeding tube armor 2010, i.e., custom made to be aligned with the vertical and horizontal offset between the feeding tube site and the stoma.

Opening 2120 is situated at one end of the feeding tube armor 2010 along the recessed portion 2110, thereby guiding and allowing the feeding tube to exit the feeding tube armor 2010. Referring to FIG. 21B illustrating an exemplary view of the back plate pad of feeding tube armor 2010, the feeding tube is looped upward from the entrance space 2190 of the armor bag face 2010 (as the armor bag face 2010 is proximate to the body of the wearer), where the entrance space 2190 corresponds with the head 2112 of the recessed portion 2110, guided through downward in the recessed portion 2110, and exits the feeding tube armor 2010 at the opening 2120 beneath the front of the armor bag face 2010. Accordingly, the feeding tube is securely positioned and guided by the recessed portion 2110 while nutrient flow within the feeding tube is unimpeded.

In one embodiment, a pad is installed on the back side of the feeding tube armor 2010 and provides security for the feeding tube hub as well as provide impact load dispersion and comfort during wear. That is, the pad is dimensioned with a slit corresponding to the recessed portion 2110 and the opening 2120 to allow the exit of the feeding tube from the armor without restricting the flow of nutrients through the feeding tube or kinking the feeding tube. In another embodiment, the pad also has an indention corresponding to entrance space 2190 configured to receive the hub of the feeding tube.

In a preferred embodiment, feeding tube armor 2010 has dimensions as follows. The feeding tube armor 2010 has a thickness of ⅜ inch (which is about half of the thickness of a typical protrusion of a feeding tube as discussed above). The length of the recessed portion 2110 including the opening 2120 is 4.5 inches. The length of the remaining portion of feeding tube armor 2010 is 1 inch.

In a preferred embodiment the feeding tube armor 2110 can be produced using injection molding, vacuum forming with composite materials using a custom made mold. Materials may include fiberglass reinforced ABS, carbon fiber and Kevlar™ or aramid fiber, heat formed Kydex™ polymer, and clear polystyrene.

Figure 22:
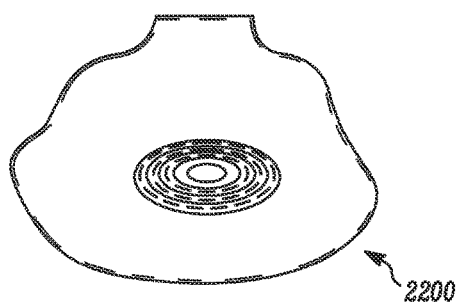
FIG. 22 illustrates an exemplary view of an ostomy appliance barrier.

FIG. 22 illustrates an exemplary view of an ostomy appliance barrier. Waste collection bag/barrier 2200 is an exemplary ostomy waste collection bag or barrier in the related art. All ostomy barriers of current manufacture are of this manner of construction. It is noted that waste collection bag/barrier 2200 is the two dimensional flat configuration representative of the related art.

It is noted that patients often have lower left and right quadrant stomas that are accompanied by scarring as a natural result of abdominal surgery in addition to existing adipose tissue. This scarring results in the third dimension or z-axis being increased from a normally appearing lower abdominal quadrant to a lower quadrant featuring dramatic curves and creases. All of the currently manufactured ostomy appliances are two dimensional, i.e., in the x-axis and y-axis dimensions and as such do not easily conform to the three dimensional landscape of typical ostomy patients.

Figure 23:
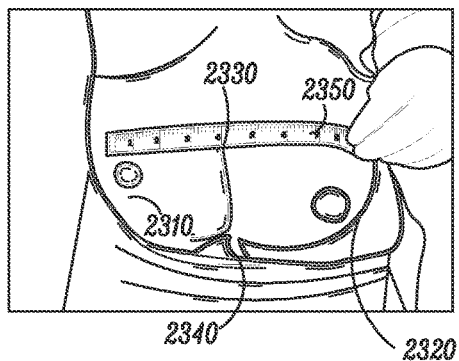
FIG. 23 illustrates an exemplary view of a patient with stomas with three-dimensional (3D) properties.

FIG. 23 illustrates an exemplary view of a patient with stomas with three-dimensional (3D) properties. Referring to FIG. 23, an exemplary view of a common adult post operative lower quadrant includes an urostomy 2310 on the lower right quadrant with normal appearance and an ileostomy 2320 on the lower left quadrant with a herniation of the abdominal area. It is noted that there is a difference in abdominal curvature between the left and right side proximal to the stomas. That is, the curvature of the urostomy 2310 is less than the curvature of the ileostomy he 2320. Mid-line scaring 2330 and 2340 also add three dimensional complexities to the dramatic landscape. Measuring tape 2350 illustrates a common measuring tape placed across the patient's abdominal quadrant providing scale in the x-axis, y-axis, and z-axis. As such, it is apparent to a common observer that two dimensional flat ostomy appliance has difficulty remaining in place and functioning. Such abdominal configuration is common among patients with one or two stomas and can frequently be much worse and extremely difficult to maintain appliance function.

As such, an embodiment of the invention is directed towards a device that is configured to fit a patient securely, comfortably in all three-dimensions. Various methods of determining a patient's three dimensional contours are generally referred to as stoma mapping. In one embodiment, an imaging device, e.g., a camera such as a high resolution camera is used on the patient to capture the stoma. In another embodiment, other devices may be utilized to capture an exact topography of the stoma and stoma region.

A method of creating a three-dimensional mold for a stoma according to an embodiment is as follows. In an embodiment, images are composed of the affected lower right or left quadrant and the immediate 4 inches directly around the stoma. A common cloth tape is used on the areas around the stoma as described. Afterward, the images are visually scaled and assessed to determine an approximation of the affected area. This collected data is then transferred to a basic framework and is used to construct a physical mold of the patient's stoma area.

In another embodiment, a direct three-dimensional molding of the patients stoma is taken, e.g., a rapid cast material. The rapid cast materials may be similar materials used in setting fractured extremities, non-toxic molding materials, and other casting materials as known now or may be later derived. In this embodiment, wet strips are applied directly onto the affected stoma area and allowed to set. After the strips have dried or cured, a positive mold is removed from the patient and reinforced with fiberglass, moldable hardening fillers, gel coat, or other similar materials may be utilized (stage 1). In stage 2 a negative mold is then constructed from stage 1 positive mold which is then used as a form for molding an ostomy appliance matching the patient.

In another embodiment, a hand held three dimensional scanner, e.g., laser scanner, is used to digitally map the patients lower left or right quadrant. The data is then collected and utilized to produce a negative mold via a three-dimensional printer. Other techniques may also be used, e.g., a three dimensional CAM file can be used to create a durable mold.

In another embodiment, data from patients are utilized to create standard molds that correspond to a group of patients with similar three-dimensional stomas. For example, a database of molds can be gathered by adding additional patient scans.

According to an embodiment, a waste collection bag attachment base may be inserted (physically, digitally, or through other methods) onto the mold that features a round concave aspect on the area directly around the stoma on the posterior aspect of the appliance. A flat platform resembling a ring approximating 50 mm in diameter and 12.6 mm across the flat resides on the anterior aspect of the appliance centered directly around the stoma opening. This is that aspect to which the waste collection bag is attached.

Figure 24A:
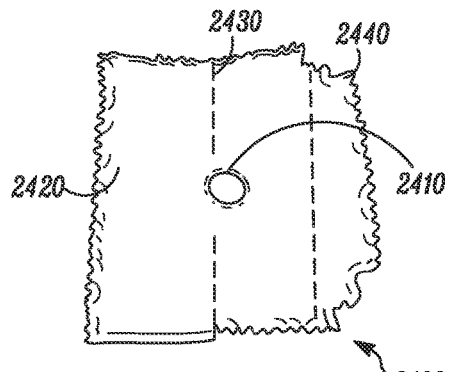
FIGS. 24A, 24B, and 24C illustrate exemplary views of a three-dimensional (3D) ostomy appliance barrier according to an embodiment.
Figure 24B:
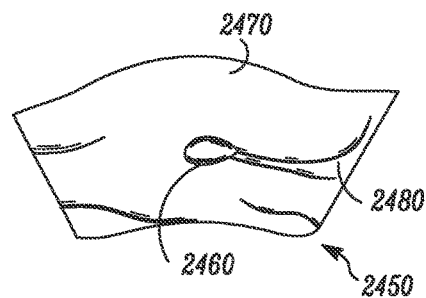
Figure 24C:
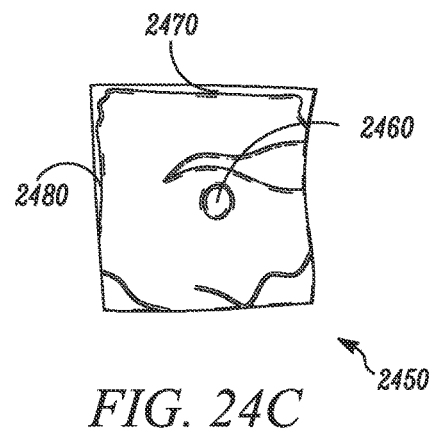

FIGS. 24A, 24B, and 24C illustrate exemplary views of a three-dimensional (3D) ostomy appliance barrier mold according to an embodiment.

Referring to FIG. 24A, an exemplary three-dimensional mold 2400 for a stoma gives a three dimensional model of a lower left or right abdominal quadrant of a patient according to an embodiment. In this embodiment, this mold 2400 was constructed by laying strips of rapid set cast material directly on to the lower left quadrant of the patient. Other casting techniques as discussed above may also be utilized. Portions 2420, 2430, and 2440 of the mold 2400 shows the curvature of the mold 2400 and the abdomen as constructed by the 3D process. In particular, portion 2410 is resulted by the curvature of the stoma as reproduced by the molding process.

Referring to FIGS. 24B and 24C, fiberglass reinforced mold 2450 is a stage 1 positive mold produced from mold 2400 by reinforcement with fiberglass. FIG. 24B illustrates the fiberglass reinforced mold 2450 as viewed from the superior aspect. FIG. 24C illustrates the fiberglass reinforced mold 2450 as viewed from a posterior aspect. The three-dimensional features of the fiberglass reinforced mold 2450 correspond with the respective features of the three-dimensional mold 2400. For example, portion 2460 of the fiberglass reinforced mold 2450 for covering the stoma correspond to portion 2410 of the three-dimensional mold In an embodiment, these molds can be utilized to construct a three-dimensional ostomy appliance or waste collection device (not shown). In this embodiment, the flange of the ostomy appliance or waste collection device would have a three-dimensional shape conforming to the relevant mold features. The flange is constructive to achieve a non-flexible final product. In one embodiment, the materials may include injection molded fiberglass reinforced ABS, composite materials, e.g., carbon fiber and Kevlar™ as described herein and other thermoplastics. The waste collection bag is communicatively coupled to the flange. Moreover, a waste wick, such as waste wick 1200, as described herein could be coupled between the flange and the waste collection bag. The waste collection bag may include durable materials, e.g., flash spun high-density polyethylene fibers, a synthetic material, PEEK, PVC, thermoplastic, polyethylene and the like, e.g., Nylon materials and Tyvek™ materials. The materials may also be further reinforced with other materials, e.g., Kevlar™ and fiberglass. The thickness of the materials is also configured to prevent inadvertent punctures, tears or cuts, thereby being much better suited for comfort, longer duration wear and resistant to hostile environments for the patient and/or other user.

In one embodiment, the three-dimensional flange is configured to be reusable with an impact resistant gel material, e.g., highly damped visco-elastic polymeric material, e.g., Sorbothane™. In this embodiment, the material is coupled to a rear surface of the three dimensional flange, e.g., the surface adjacent the abdomen. The opposite surface of the flange includes an attachment feature to allow it to be coupled to a waste collection bag. The attachment feature may include an adhesive, adhesive and flange, or other coupling mechanism as known now may be later derived in the art.

In another embodiment, the 3D molds (either digitized, i.e., as a CAM file, or physical, i.e., molds 2400 and 2450) of the stoma may be adapted to be used for other customized devices for the stoma. For example, the 3D molds may be adapted to form the base plate 110 and/or plate pad 120 of ostomy armor 100, waste wick 1200, and/or protection system 2000. In an embodiment, the customized devices may be made from molds that are based on the 3D molds. For example, the base plate 110 may include additional dimensions and tolerances over the measurement of the 3D mold, i.e., the base plate 110 may need to be bigger than the 3D mold to accommodate other accessories such as plate pad 120. A customized mold may be developed based on the 3D mold using computer methods for a digitalized mold to physical methods for a physical mold or using other means as now known or may be later derived.

In an embodiment, a 3D scanner may be used to scan a patient's stoma area to produce a direct likeness in any properly equipped desk top or laptop containing 3D modeling software. The likeness can then be inverted and sent to a 3D printer where a negative mold is then constructed and used to fabricate a 3D ostomy appliance. In another embodiment, the 3D printer may directly print a 3D ostomy appliance using the digitized mold.

Figure 25A:
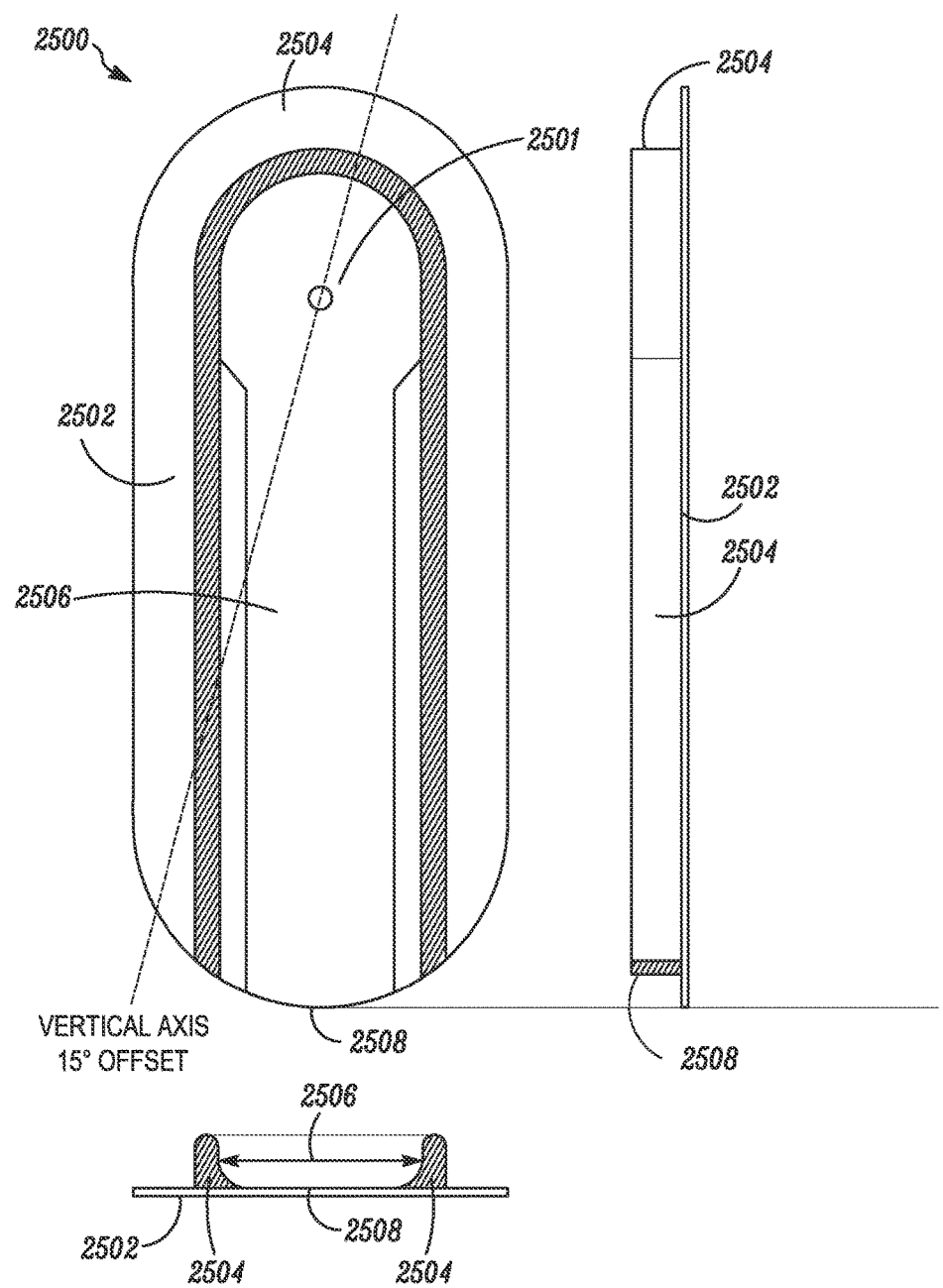
FIGS. 25A and 25B illustrate exemplary views of a waste collection bag protection apparatus according to an embodiment.
Figure 25B:
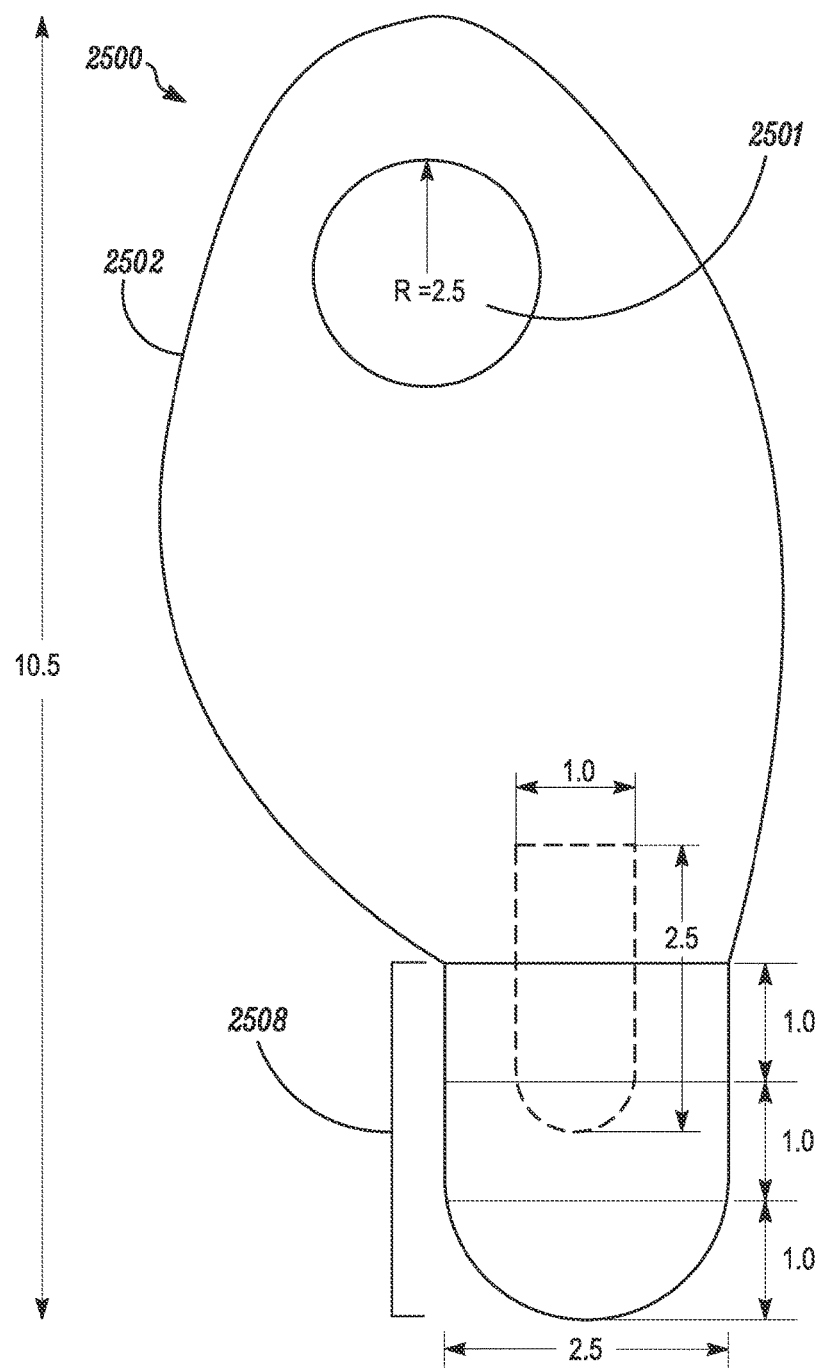

FIGS. 25A and 25B illustrate exemplary views of a waste collection bag protection apparatus according to an embodiment.

Waste collection bag 2500 utilizes an end closure that can be opened to empty the contents of the bag, thereby making the bag reusable. The waste collection bag 2500 may be constructed from durable materials as disclosed herein to allow sustained use in hostile environments, e.g., excessive heat, excessive impacts, physical stress. Moreover, the waste collection bag 2500 may include a scented material to avoid any unwanted odors. In a preferred embodiment, the waste collection bag 2500 does not include any vents. The waste collection bag 2500 may be shaded to mimic the natural pigment of a person's skin.

The waste collection bag 2500 includes an opening 2501, e.g., having a 50 mm diameter allowing an end user to properly fit the opening over at least a portion of a stoma. The waste collection bag 2500 also includes a raised ridge 2504 extending from the opening 2501 to an end portion of the bag 2508. In a preferred embodiment, the raised portion 2504 curves around the opening 2501. The end of the bag 2508 includes a heavy duty three fold bottom closure to prevent rupture, e.g., 1 inch by 2.5 inch reinforcements constructed from semi-rigid material, e.g., thermoplastic, nylon, Delrin™, which are bonded to the flexible outer bag. In addition, an external tab is utilized with the closure system to allow for rapid and/or easy opening and closing of the three-fold bottom closure. In a preferred embodiment, a tab is includes a MIL Spec type II Class I hook and pile tape closure.

The raised ridge 2504 creates a protective channel region 2506 that allows waste from the stoma to enter the waste collection bag 2500 through the opening 2501 in an obstructed manner. For example, should external pressure be placed on the bag 2500, the protective channel 2506 permits unobstructed flow as the raised ridge 2504 defines a consistent volume of the waste collection bag 2500, i.e., the flattening of the waste collection bag 2500 is minimized. In contrast with the raised ridge 2504, the side 2502 demarks the side edge of the waste collection bag 2500.

Referring to FIG. 25B, an overall container shape of the waste collection bag 2500 is illustrated according to an embodiment of the invention. The upper aspect of the container minimizes material around the opening 2501 and is offset laterally from center with the overall container length set at 10.5 inches. The opening 2501 has a radius of 2.5 mm.

The bottom face of the bag 2508 illustrates the rear inner container molding. This inner molding provides an unobstructed pathway for waste flow into the container which cannot be blocked by any outer garments or physical position of the patient. Also, the bottom of the bag 2508 has an alignment of approximately 15 degree in vertical orientation in relation to the container opening 2501. As such, in this embodiment, bag 2500 has a sufficiently diagonally aligned waste flow channel from the opening 2501 to the bottom face 2508.

In one embodiment, a rigid vacuum may be formed at the upper bag front 2504. This component is bonded to the inside front face of the top of the waste collection bag 2500.

A method of making the waste collection bag 2500 is as follows. High pressure heat bonding using machined press dies at approximately 1500 psi may be used to form and bond the various parts of the waste collection bag 2500. Several bonding process steps in proper order will ensure the parts are bonded to produce a completed assembly containing all of the correct components.

FIG. 26 illustrates an exemplary view of an emergency leak and blowout kit (EBOK) according to an embodiment. EBOK 2700 is a highly portable emergency leak and blowout medical kit to minimize worry concerning leaks of an ostomy appliance away from home. As such, EBOK 2700 mitigates embarrassment from leakage and blowouts while in public or otherwise away from home. EBOK 2700 is also a kit that contains all of the components necessary to change an ostomy appliance as well as protecting the patient from further contamination as well as clean up and mitigation of the existing mess.

According to an embodiment, EBOK 2700 includes two styles: one for Ileostomy/Colostomy, and one for Urostomy. In another embodiment, the EBOK 2700 may also include components of each style as one combined kit. For example, EBOK 2700 may include, as one combined kit, non-duplicated component for each style, while containing only one of the duplicated components.

In an embodiment, the differences between the two styles of kits is that the ostomy appliance contained in the red "Colostomy/Ileostomy" is a common appliance for colostomy, whereas the ostomy appliance contained in the blue "Urostomy" kit is specifically intended for those patients with a diverted ureter.

Referring to FIG. 26, an exemplary EBOK 2700 includes one or more of the following items: an instructions for use 2710, a collection barrier 2730, a scissors (straight or round-nosed) 2740 used for enlarging the opening in the ostomy appliance as needed, an adhesive remover wipe 2750 to remove residual adhesive from the old ostomy appliance, a skin prep wipe 2760 for applying a light tack solution to aid in adhesion of the new ostomy appliance, one or more (preferably four) large paper towels 2770 for bulk pick up of exposed waste, a packet of baby wipes 2780 for detailed clean-up of exposed waste, a disposable apron 2790 for preventing further contamination of clothing, a disposable nitrile gloves 2792 for preventing propagation of waste and protect the patients hands while replacing the ostomy appliance, and a waste disposal bag 2794 to place all of the contaminated components into for disposal.

The contents of the EBOK 2700 are sealed in a color coded container 2720. For example, the container may be colored red for colostomy and ileostomy and blue for urostomy. The container is preferably sized to fit all contents while sized to be portable. In one embodiment, the color coded container 2720 may be resealable and reuseable (i.e., the content of the package is opened for demonstration purpose or during a false alarm).

In another embodiment, specific component manufacturers may vary, and other suitable materials with similar properties may be substituted. For example, other types of wipes suitable for human skin may be used in place of the packet of baby wipes 2780. In a further embodiment, other specific components may be added to EBOK 2700 as now known or may be later derived.

The present disclosure, in various aspects, embodiments, and/or configurations, includes components, methods, processes, systems and/or apparatus substantially as depicted and described herein, including various aspects, embodiments, configurations embodiments, subcombinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation.

The foregoing discussion has been presented for purposes of illustration and description. The foregoing is not intended to limit the disclosure to the form or forms disclosed herein. In the foregoing description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this description, with each claim standing on its own as a separate preferred embodiment of the disclosure.

Moreover, though the description has included a description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A medical apparatus, comprising:
a base plate comprising a convex curved outer surface, a concave curved inner surface wherein each of the entire convex curved outer surface and the entire concave curved inner surface form a substantially planar curved structure that is configured to be substantially similar to a curvature of an abdominal area of a user where the base plate is configured to reside, a top side, a bottom side, a right side, a left side, the right side is substantially perpendicular to the bottom side and the top side, the left side comprises a first angle extending from the bottom side to the top side, the first angle is in a range from about thirty degrees to about seventy five degrees, a first cutout extending through the base plate and a second cutout extending through the base plate, each of the first cutout and the second cutout are arranged within an interior dimension of the base plate, the base plate is dimensioned to substantially cover at least a stoma, an adjacent abdomen region of a user, and at least an upper portion of a waste collection bag when in use;
a plate pad comprising a soft flexible foam material, the plate pad is non-releasably attached to a back surface of the base plate, the plate pad having an external dimension substantially identical to the base plate, the plate pad comprising a cutout region, the cutout region includes a channel region sized to be narrower at an upper portion of the channel region and wider at a lower portion of the channel region, the upper portion of the channel region is closed and the lower portion of the channel region is open, wherein the base plate and plate pad are configured to prevent or minimize herniation of a stoma or ostomy site and accommodate existing hernias by contact of the plate pad across a surface of the abdominal area; and
a belt comprising a first piece and a second piece, the first piece of the belt comprising a first end fixedly attached to the first cutout and a second end coupled to a first attachment mechanism, the second piece of the belt comprising a first end fixedly attached to the second cutout and a second end coupled to a second attachment mechanism, wherein the first attachment mechanism and the second attachment mechanism are configured to releasably couple to each other.

2. The medical apparatus of claim 1, wherein the plate pad further comprises a plate pad cover.

3. The medical apparatus of claim 2, wherein the plate pad cover comprises one or more of a chamois material, microfiber material, terry cloth material, and cotton jersey knit material.

4. The medical apparatus of claim 1, wherein the belt further comprises a waist pad extending from a portion of the belt, the waist pad comprising a foam material, a rigid backing on a portion of the foam material, and a soft cover.

5. The medical apparatus of claim 1, wherein the first attachment mechanism comprises a female connector and the second attachment mechanism comprises a male connector.

6. The medical apparatus of claim 1, wherein the base plate comprises an aluminum material.

7. The medical apparatus of claim 3, wherein the base plate comprises a titanium material.

8. The medical apparatus of claim 1, wherein the base plate comprises a logo arranged on a surface of the base plate.

9. The medical apparatus of claim 1, wherein the base plate comprises one or more layers of composite materials.

10. The medical apparatus of claim 1, wherein a face of the base plate comprises one or more of a color finish and a marking.

11. The medical apparatus of claim 1, wherein the base plate in operation is configured to prevent or minimize herniation of a stoma or ostomy site and accommodate existing hernias.

12. The medical apparatus of claim 1, wherein the cutout region has a keyhole type geometry.

13. A method of making an ostomy apparatus, comprising the steps of:
forming a substrate material into a base plate having a dimension to cover a stoma of a user and at least a portion of a waste collection bag, the base plate comprising a convex curved outer surface, a concave curved inner surface, wherein each of the entire convex curved outer surface and the entire concave curved inner surface have a curvature configured to be substantially similar to a curvature of an abdominal area of a user where the base plate is configured to cover, a top side, a bottom side, a right side, a left side, the right side is substantially perpendicular to the bottom side and the top side, the left side comprises a first angle extending from a bottom most portion of the bottom side to a top most portion of the top side, the first angle is in a range from about thirty degrees to about seventy five degrees, a first cutout extending through the base plate and a second cutout extending through the base plate, each of the first cutout and the second cutout are arranged within an interior dimension of the base plate;

forming a soft compressible flexible foam plate pad including an external dimension substantially identical to the base plate, the plate pad comprising a cutout region, the cutout region includes a channel region sized to be narrower at an upper portion of the channel region and wider at a lower portion of the channel region, the upper portion of the channel region is closed and the lower portion of the channel region is open, wherein the base plate and plate pad are configured to prevent or minimize herniation of a stoma or ostomy site and accommodate existing hernias by contact of the plate pad on the abdominal area;

non-releasably attaching the plate pad to a back side of the base plate;

attaching a first end of a first belt piece to the first cutout of the base plate;

attaching a second end of the first belt piece to a first attachment mechanism;

attaching a first end of a second belt piece to the second cutout of the base plate; and attaching a second end of the second belt piece to the second attachment mechanism.

14. The method of claim 13, wherein the forming the substrate into a base plate comprises the steps of laser cutting the substrate material.

15. The method of claim 14, further comprising the step of marking a surface of the base plate with information indicative of one or more of make, model, serial number, trademark, informational notice, and warning notice.

16. The method of claim 15, wherein the marking step comprises the step of laser etching.

17. The method of claim 14, wherein the substrate material comprises a material selected from the group consisting of aluminum, titanium, and combinations of the same.

18. A medical apparatus, comprising:

a first base plate comprising a convex curved outer surface, a concave curved inner surface, a top side, a bottom side, a right side, a left side, the right side is substantially perpendicular to the bottom side and the top side, the left side comprises a first angle extending from the bottom side to the top side, the first angle is in a range from about thirty degrees to about seventy five degrees, a first cutout extending through the base plate and a second cutout extending through the base plate, each of the first cutout and the second cutout are arranged within an interior dimension of the base plate, the base plate is dimensioned to substantially cover at least a first stoma, an adjacent abdomen region of a user, and at least an upper portion of a first waste collection bag when in use;

a first plate pad comprising a flexible material, the plate pad adhered to a back surface of the base plate, the plate pad having an external dimension substantially identical to the base plate, the plate pad comprising a cutout region, the cutout region includes a channel region sized to be narrower at an upper portion of the channel region and wider at a lower portion of the channel region, the upper portion of the channel region is closed and the lower portion of the channel region is open;

a second base plate comprising a second convex curved outer surface, a second concave curved inner surface, a second top side, a second bottom side, a second left side and a second right side, the base plate is dimensioned to substantially cover at least a portion of a second stoma, an adjacent abdomen region of a user, and at least an upper portion of a second waste collection bag when in use; and a connection unit having a first end and a second end, the first end is attached to the right side of the first base plate and the second end is attached to a second right side of the second base plate, wherein the connection unit is adjustable to permit adjustment of a separation between the first base plate and the second base plate in an x-axis direction and also adjustment of a separation in a y-axis direction such that the first base plate can be arranged substantially over the first stoma and the second base plate can be arranged over the second stoma, the first stoma is positioned at a different x-y location from the second stoma.

19. The medical apparatus of claim 18, wherein the first plate pad comprises an open celled foam material.

20. The medical apparatus of claim 18, wherein the second plate pad comprises an open celled foam material.

21. The medical apparatus of claim 18, wherein the first base plate and the second base plate is made using a three-dimensional mold and at least partially vacuum formed from the mold.

22. The medical apparatus of claim 18, wherein the first base plate and second base plate in operation are configured to prevent or minimize herniation of a stoma or ostomy site.

23. The medical apparatus of claim 18, wherein the first base plate and the second base plate comprise a composite material.

24. The medical apparatus of claim 1, further comprising a waste wick comprising an absorbent material.

25. The medical apparatus of claim 1, further comprising a waste collection bag comprising a three-dimensional flange.

26. The medical apparatus of claim 25, wherein the three-dimensional flange comprises a gel material and is reusable.

27. The medical apparatus of claim 24, wherein the absorbent material comprises a cellulose material.

* * * * *